US009468730B2

(12) United States Patent
Worley

(10) Patent No.: US 9,468,730 B2
(45) Date of Patent: Oct. 18, 2016

(54) VENTILATOR TO TRACHEOTOMY TUBE COUPLING

(75) Inventor: Brian D. Worley, Tulsa, OK (US)

(73) Assignee: Lazarus Medical, LLC

( * ) Notice: Subject to any disclaimer, the term of this patent is extended or adjusted under 35 U.S.C. 154(b) by 2734 days.

(21) Appl. No.: 11/899,221

(22) Filed: Sep. 5, 2007

(65) Prior Publication Data

US 2008/0041391 A1 Feb. 21, 2008

Related U.S. Application Data

(63) Continuation-in-part of application No. 11/731,538, filed on Mar. 30, 2007, now Pat. No. 8,485,193, which is a continuation-in-part of application No. 11/348,199, filed on Feb. 6, 2006, now abandoned.

(51) Int. Cl.
| | | |
|---|---|---|
| *A62B 9/06* | (2006.01) | |
| *A61M 16/04* | (2006.01) | |
| *A61M 16/08* | (2006.01) | |

(52) U.S. Cl.
CPC ..... *A61M 16/0465* (2013.01); *A61M 16/0427* (2014.02); *A61M 16/0488* (2013.01); *A61M 16/0434* (2013.01); *A61M 16/0816* (2013.01)

(58) Field of Classification Search
USPC .......... 128/200.26, 202.28, 207.17, 207.15, 128/207.16, 911, 912, DIG. 26, 202.27, 128/207.14, 207.29; 403/263, 326, 329, 403/361; 285/93, 319, 332, 38, 307
See application file for complete search history.

(56) References Cited

U.S. PATENT DOCUMENTS

| | | | |
|---|---|---|---|
| 3,374,856 A | | 3/1968 | Wirt |
| 3,388,705 A | * | 6/1968 | Grosshandler ........... 128/207.14 |
| 3,707,301 A | | 12/1972 | Rauls |
| 4,307,903 A | | 12/1981 | Wallace |
| 4,449,523 A | | 5/1984 | Szachowicz et al. |
| 4,817,598 A | | 4/1989 | LaBombard |
| 4,909,248 A | | 3/1990 | Anderson |
| 5,251,616 A | | 10/1993 | Desch |
| 5,282,463 A | | 2/1994 | Hamersley |
| 5,357,952 A | | 10/1994 | Schuster et al. |
| 5,458,139 A | | 10/1995 | Pearl |
| 5,460,176 A | | 10/1995 | Frigger |
| 5,464,011 A | | 11/1995 | Bridge |
| 5,606,966 A | | 3/1997 | Smith |
| 5,645,048 A | * | 7/1997 | Brodsky et al. ......... 128/202.27 |
| 5,782,236 A | | 7/1998 | Ess |
| 5,864,938 A | * | 2/1999 | Gansel et al. .................. 29/506 |

(Continued)

OTHER PUBLICATIONS

International Search Report and Written Opinion (PCT/US08/03616) issued by the International Searching Authority (ISA/US), dated Aug. 26, 2008; 11 pgs.

(Continued)

*Primary Examiner* — Justine Yu
(74) *Attorney, Agent, or Firm* — Frank J. Catalano; Gable Gotwals

(57) ABSTRACT

A coupling for connecting an air supply to a respiratory support device has a latching mechanism which prevents the coupling from inadvertently axially displacing from the respiratory support device after they have been mated in a pneumatically discrete path. Non-axial forces are used to disengage the coupling from the respiratory support device. The coupling may include a trailing end adapter which permits rotation of the coupling relative to the air supply rather than to the respiratory support device.

2 Claims, 22 Drawing Sheets

(56) References Cited

U.S. PATENT DOCUMENTS

| | | | |
|---|---|---|---|
| 6,029,668 A | 2/2000 | Freed | |
| 6,099,519 A * | 8/2000 | Olsen et al. | 604/534 |
| 6,135,111 A | 10/2000 | Mongeon | |
| 6,248,099 B1 | 6/2001 | Bell | |
| 6,398,266 B1 * | 6/2002 | Crump | 285/226 |
| 6,484,724 B1 | 11/2002 | Sloan | |
| D466,607 S * | 12/2002 | Cise et al. | D24/110 |
| 6,505,866 B1 * | 1/2003 | Nakamura et al. | 285/423 |
| 6,588,426 B2 | 7/2003 | Linderoth | |
| 6,612,309 B1 | 9/2003 | Ancona | |
| 6,725,862 B2 | 4/2004 | Klinberg et al. | |
| 6,769,430 B1 * | 8/2004 | Carlsen et al. | 128/201.13 |
| 6,802,316 B1 | 10/2004 | Fulgham | |
| 6,971,684 B2 * | 12/2005 | Ferrari | 285/319 |
| 7,341,061 B2 * | 3/2008 | Wood | 128/207.29 |
| 2005/0161047 A1 | 7/2005 | Briggs, III | |
| 2005/0166924 A1 | 8/2005 | Thomas et al. | |
| 2007/0181130 A1 | 8/2007 | Worley | |

OTHER PUBLICATIONS

International Preliminary Report on Patentability (PCT/US07/02412) issued by the International Bureau, dated Aug. 21, 2008; 7 pgs.

International Search Report and Written Opinion (PCT/US08/10344); issued by the International Seaching Authority (ISA/US) on Nov. 10, 2008; 8 pages.

International Preliminary Report of Patentability issued by the International Bureau on Mar. 18, 2010 in PCT/US2008/010344 (5 pages).

International Search Rpt., Oct. 23, 2007.

* cited by examiner

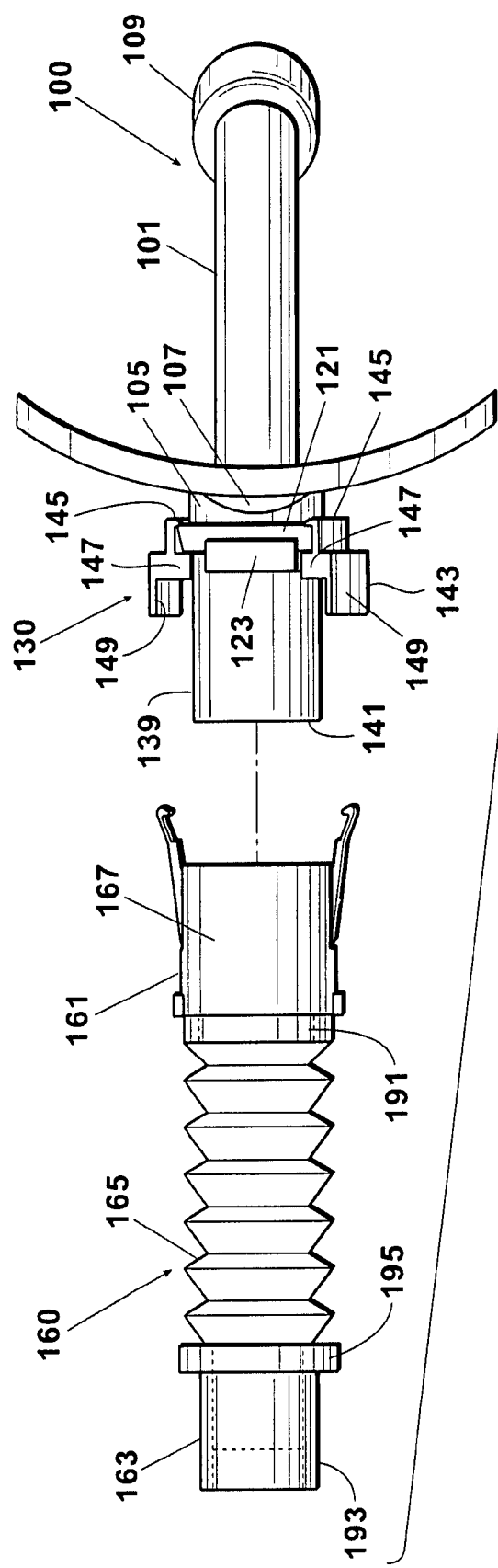
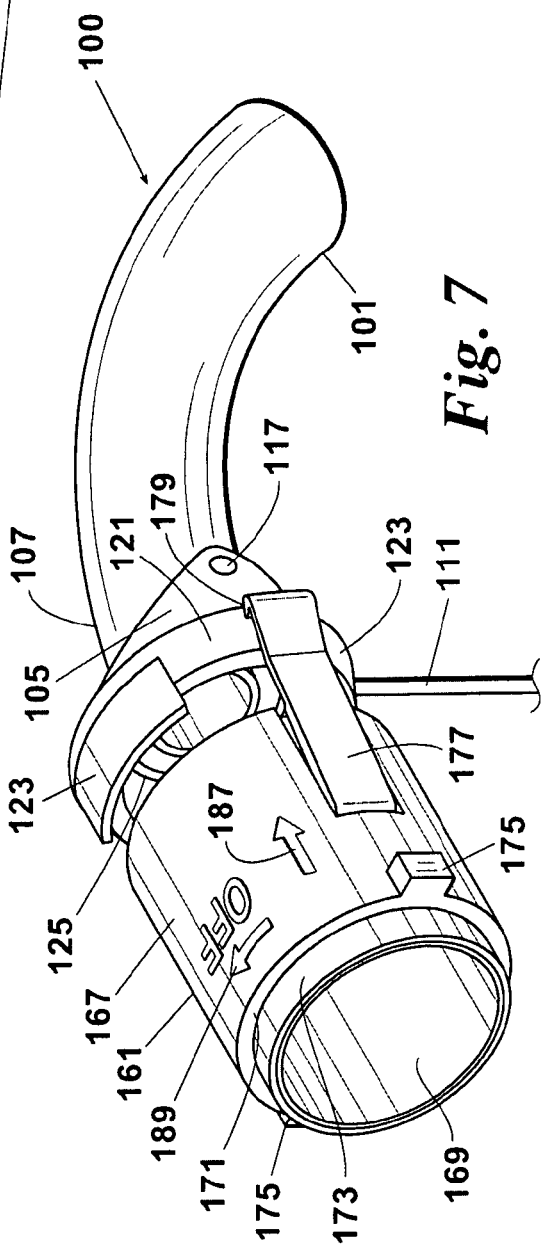
Fig. 5
Fig. 7

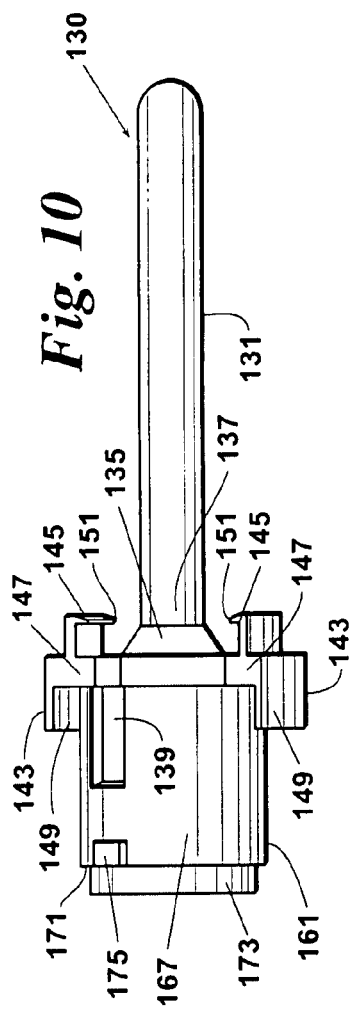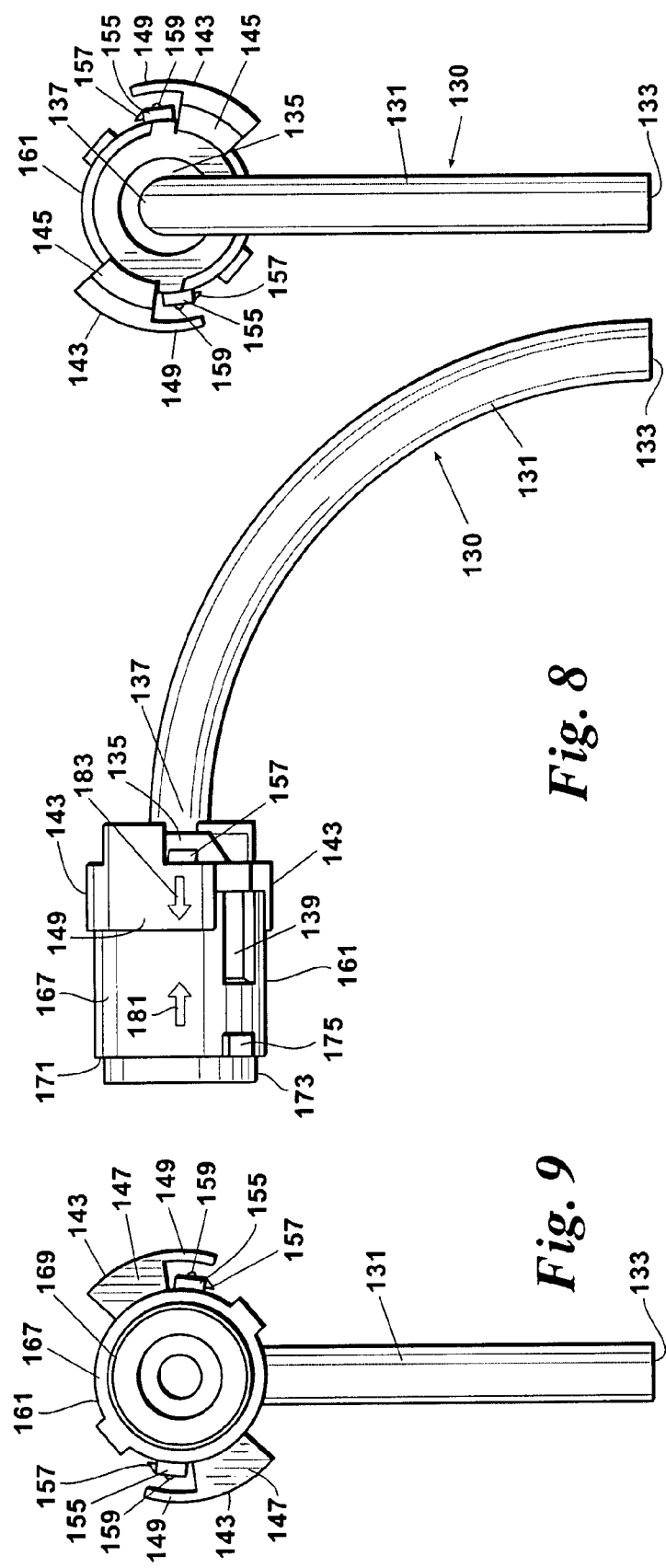

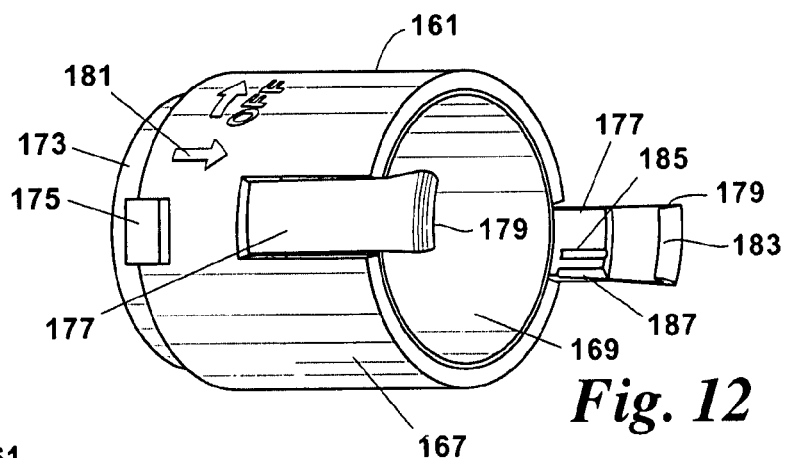
*Fig. 12*
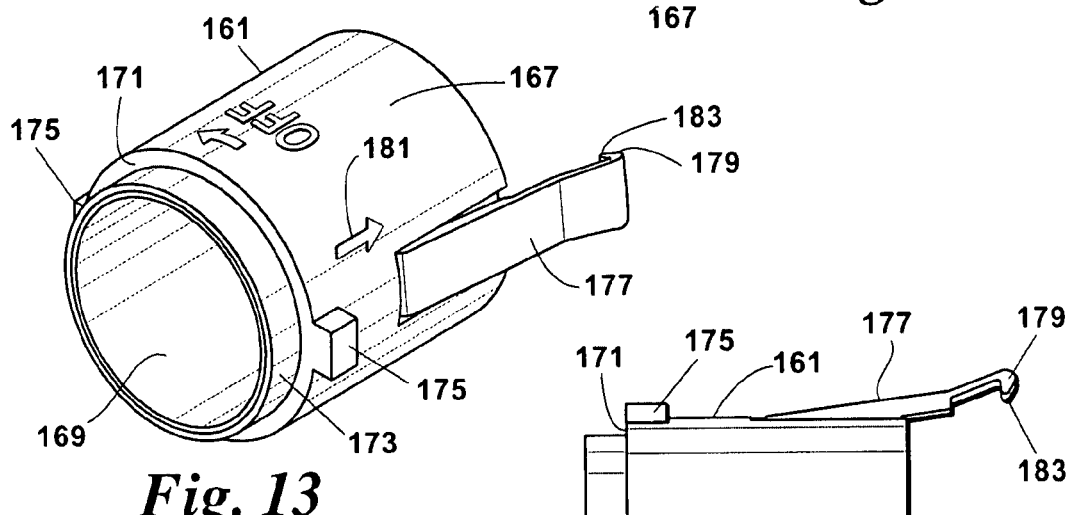
*Fig. 13*
*Fig. 16*
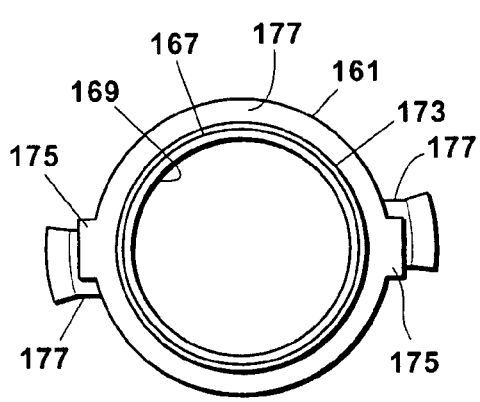
*Fig. 15*
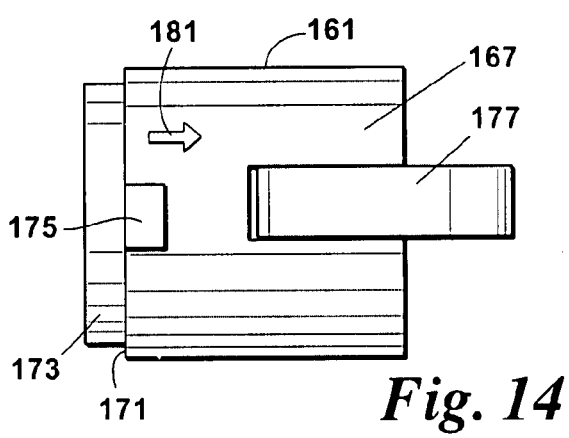
*Fig. 14*

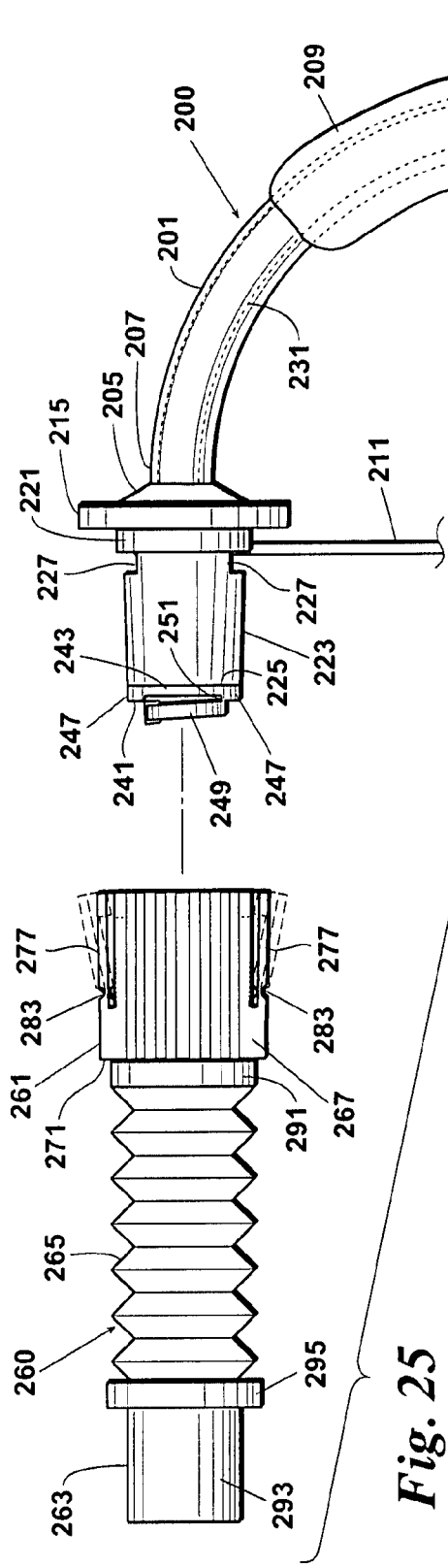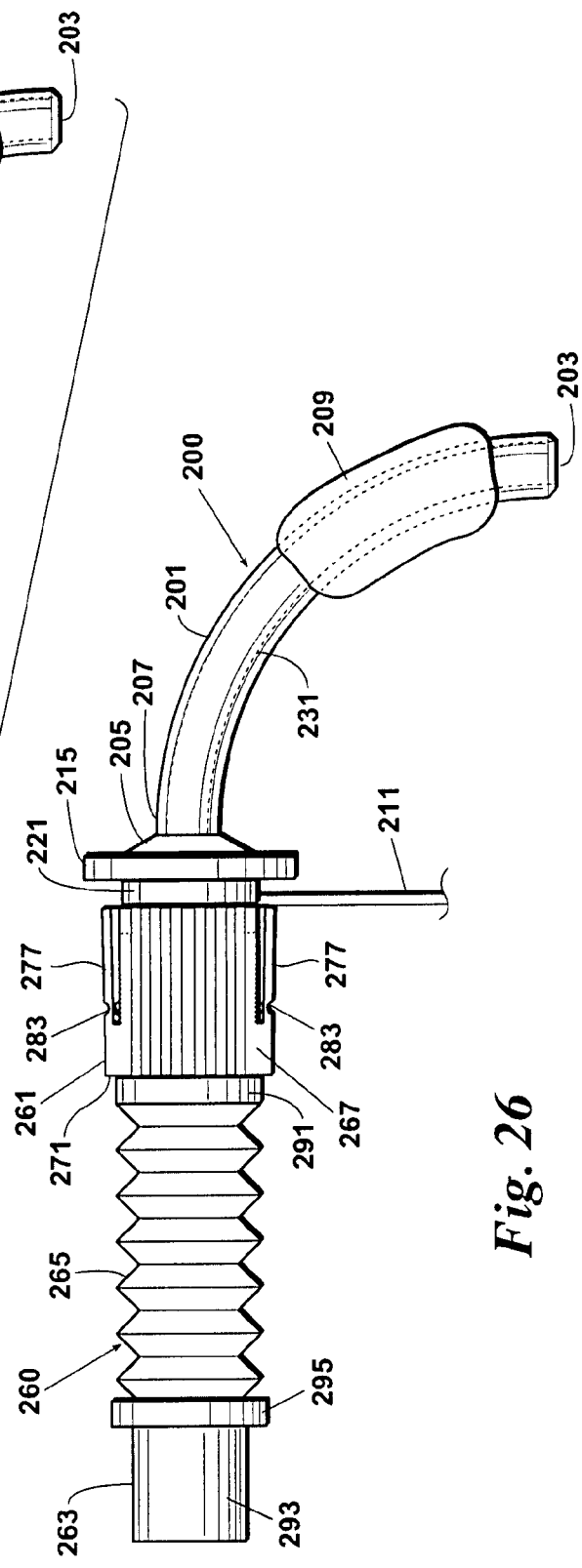
Fig. 25
Fig. 26

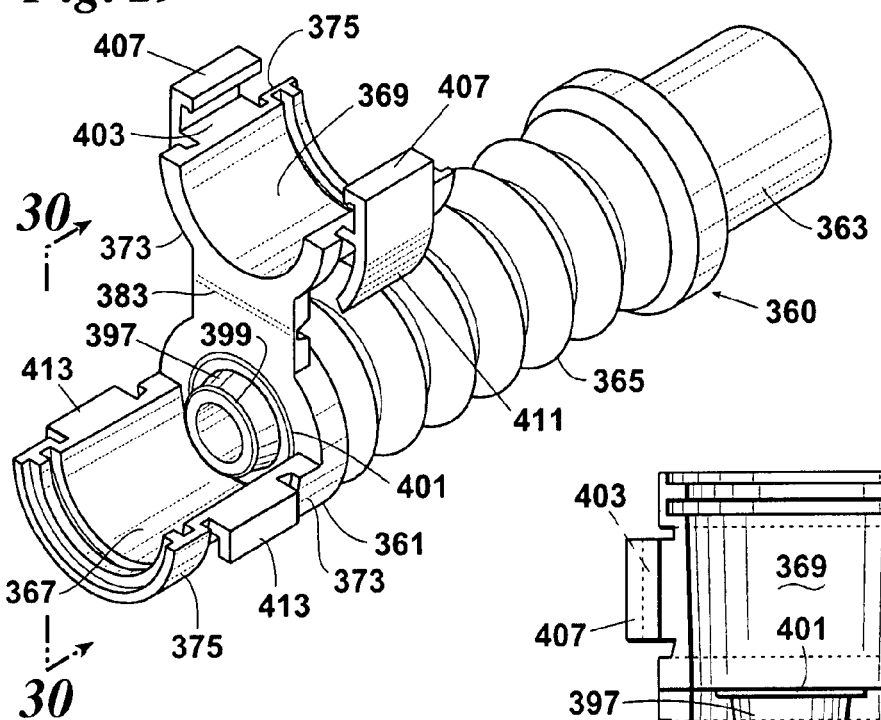
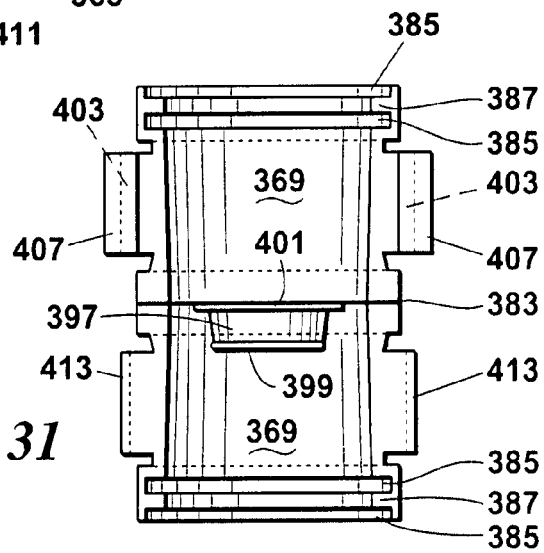
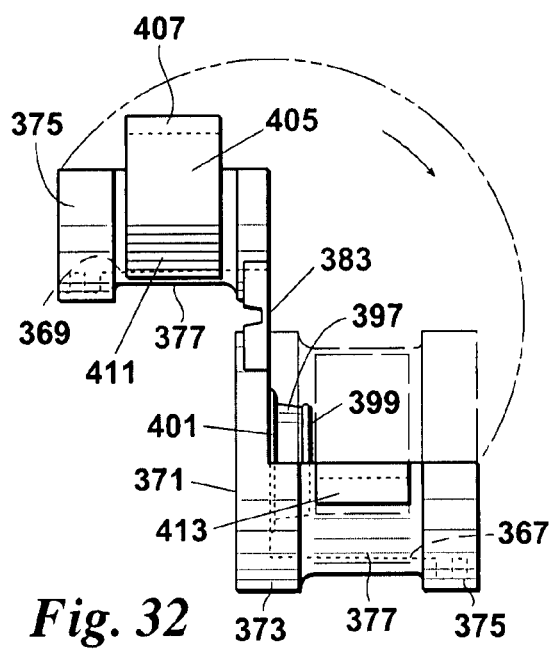
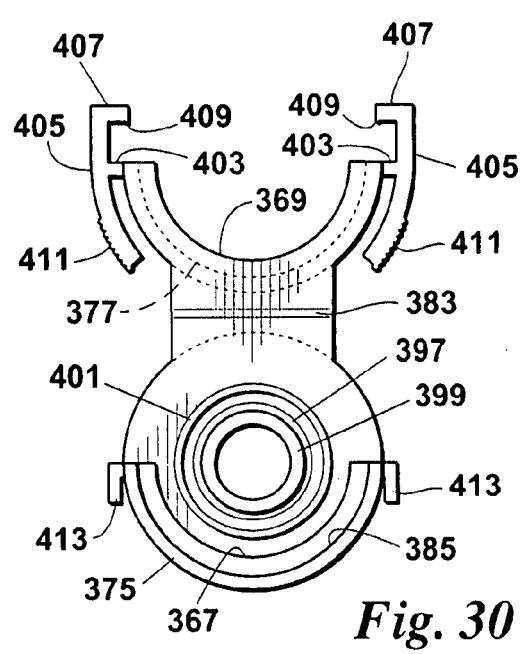

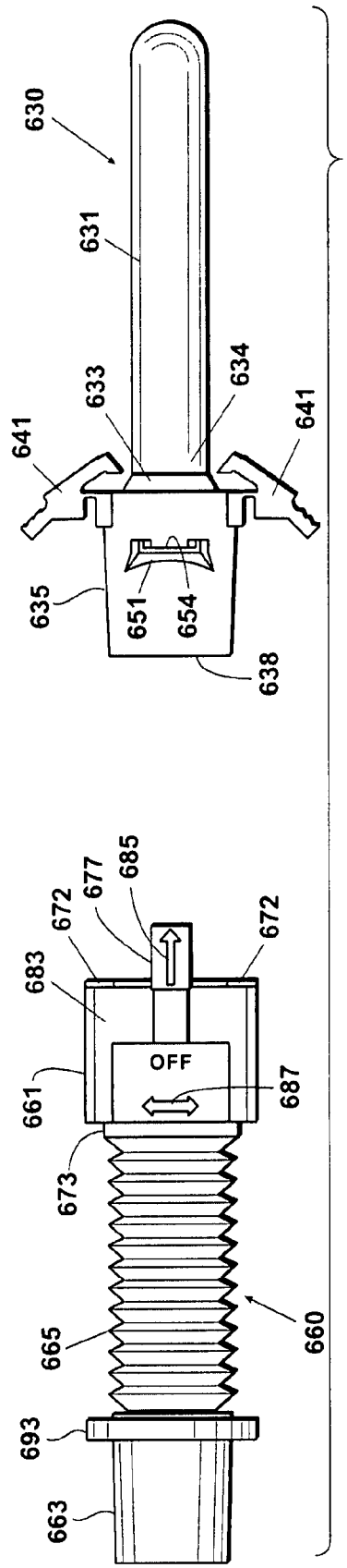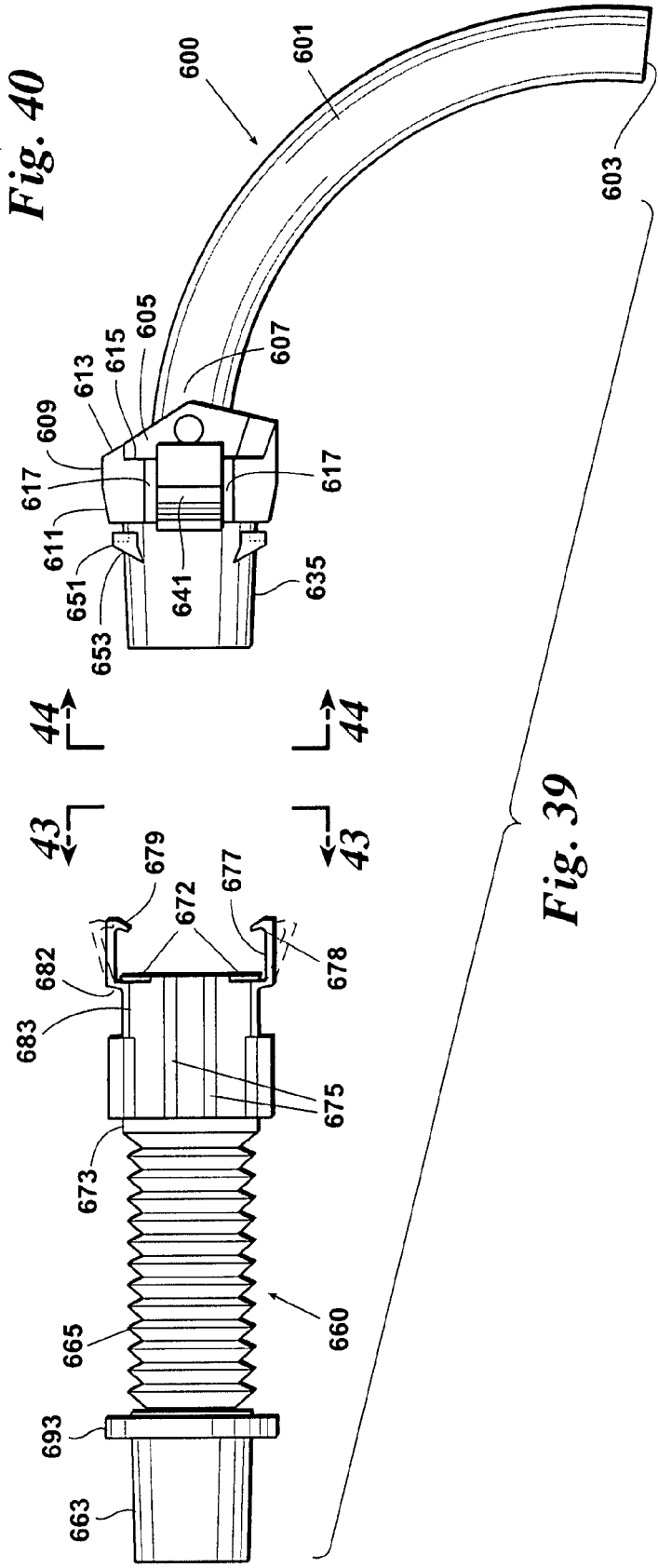

VENTILATOR TO TRACHEOTOMY TUBE COUPLING

REFERENCE TO PENDING APPLICATIONS

This application is a continuation-in-part application claiming priority to U.S. patent application Ser. No. 11/731,538 filed Mar. 30, 2007, entitled Ventilator to Tracheotomy Tube Coupling which is a continuation-in-part application claiming priority to U.S. patent application Ser. No. 11/348,199, filed Feb. 6, 2006, entitled Ventilator to Tracheotomy Tube Coupling.

REFERENCE TO MICROFICHE APPENDIX

This application is not referenced in any microfiche appendix.

BACKGROUND OF THE INVENTION

This invention relates generally to medical equipment and more particularly concerns devices used to connect ventilators to tracheotomy tubes.

For adult patients, two-piece tracheotomy tubes having inner and outer cannulas are presently in common use. The outer cannula is inserted into the patient's windpipe and the inner cannula is inserted into or removed from the outer cannula for use or for replacement, cleaning or disinfecting, respectively. The outer cannula of these two-piece devices has a collar on its trailing end which is configured to be positively engaged with a collar on the leading end of the inner cannula. The cannulas cannot be disengaged from each other affirmative release of their positive engagement. The trailing end of the combined cannulas has a tapered tubular extension which plugs into or into which is plugged, depending on the diameter of the tubular extension of the particular tracheotomy tube, the leading end of a flexible connector. The trailing end of the flexible connector is connected to a tube extending from the ventilator or other external equipment. The present tapered tubular extension connection to the ventilator is dependent on mere insertion of a tapered tube into a constant diameter tube in the hope of achieving a snug fit. To assist in making this connection, the flexible connectors have annular flanges with significantly wider diameters than the tubular portions of the connectors so as to facilitate manipulation of the connectors with the thumb and forefinger.

For children, a smaller, one piece tracheotomy tube is made from a very soft, pliant material. The entire tracheotomy tube must be frequently removed, at least once a week, from the child's trachea, cleaned and disinfected and reinserted into the trachea. The same flanged flexible connector used with the adult devices is also used with the children's devices. The tapered tubular extension of the children's tracheotomy tube is integral with the pliant tracheotomy tube and has a hard plastic outer sleeve which is inserted directly into the flexible connector. An annular flange on the trailing end of the tubular extension of the child's tracheotomy tube holds the hard plastic sleeve in place on the extension.

Because of their structural configuration and operational steps, there are some problems inherent in the known one or two piece tracheotomy tubes, in the known flexible connectors and in their combination.

One set of problems is related to the comfort of the patient. The profile of the flanged flexible connectors, falling generally between the underside of the patient's chin and the patient's chest, fosters a breakdown of skin and tissue on the chin or chest, depending on the head movements of the patient. This is especially true for children, their chin-to-chest cavity being comparatively small. This concern is sometimes addressed by after-market removal of all or a portion of the flange, but this solution generally results in a damaged connector, increasing the likelihood of infection-causing secretions and also becomes less secure due to removal of the firm portion of the connector. Also, the manipulation of the flange to connect or disconnect the connector to or from the tubular extension can cause considerable discomfort to the patient, since this often requires the application of manual pressure to the patient's neck, chin or chest. It is common practice to extend rubber bands from one side of a neck plate on the tracheotomy tube collar to the flexible connector and back to the other side of the neck plate in an effort to hold the flexible connector in place, but the rubber bands are likely either too elastic or too inelastic to properly accomplish this purpose. While a child's tracheotomy tube is smaller than an adult's, the available space between the chin and chest is significantly smaller and the flexible connector flange is the same size as used for adults, so the smaller device affords no relief for the connector flange related comfort problems. And, since the child's tracheotomy tubes are of one piece construction, the force necessary to disconnect the flexible connector may be directly applied to the patient's neck or windpipe.

A second set of problems is related directly to the ability, or inability, of the system to accomplish its primary purpose of keeping the patient's trachea connected to the ventilator. To begin with, tapered connections tend to easily separate in the best of circumstances, there being minimal surface contact between the tapered and constant diameter components. Moreover, the connector and tracheotomy tube parts are always wet and slippery due to the very nature of their application and are not very tightly mated because of the neck pressure problems. The end result is a connection so tenuous that a mere sneeze, cough or turn or tip of the head can cause the connector and the tapered tubular extension to separate, defeating the operation of the system. Even without a sneeze, cough, turn or tip, the flange itself functions as a lever against the chin or chest in response to the patient's head movements, and the reciprocal levering by the flange will eventually cause the connector and the tubular extension to disconnect.

A third set of problems concerns the performance of the medical staff as a result of these other problems. The inherent comfort issues result in more pains-taking, time-consuming effort by the staff in an effort to reduce the impact of these discomforts on the patient. And, because of the ease of inadvertent disconnection of the system, the staff unnecessarily spends valuable time monitoring and reconnecting the connectors to the tubular extensions of the tracheotomy tubes.

It is, therefore, a primary object of this invention to provide an improved tracheotomy tube coupling. Another object of this invention is to provide a tracheotomy tube coupling which reduces a likelihood of associated patient discomfort. It is also an object of this invention to provide a tracheotomy tube coupling which is more suitably profiled for positioning between a patient's chin and chest. Still another object of this invention is to provide a tracheotomy tube coupling which is profiled to reduce a likelihood of skin or tissue breakdown on a patient's chin and chest. A further object of this invention is to provide a tracheotomy tube coupling which simplifies manipulation of the coupling in relation to the patient. Yet another object of this invention to provide a tracheotomy tube coupling which reduces a likelihood of exertion of discomforting pressure on the chin, neck, chest or windpipe of a patient during connection or disconnection of the coupling from the tracheotomy tube. An additional object of this invention is to provide a tracheotomy tube coupling which makes inadvertent disconnection of the tracheotomy tube from the connected medical equipment less likely. Another object of this invention is to provide a tracheotomy tube coupling which does not rely on tapered to constant diameter connections to maintain connection between the tracheotomy tube and its related equipment. It is also an object of this invention to provide a tracheotomy tube coupling which is profiled to reduce a likelihood that the coupling will operate as a self-disconnecting lever. Still another object of this invention to provide a tracheotomy tube coupling which can be easily connected and disconnected from the tracheotomy tube by the medical staff. A further object of this invention is to provide a tracheotomy tube coupling which can reduce the time expended by the medical staff to monitor and maintain the coupling connections. Yet another object of this invention is to provide a tracheotomy tube coupling which facilitates more rapid disassembly and reassembly of associated components from the tracheotomy tube for cleaning and disinfecting purposes.

SUMMARY OF THE INVENTION

In accordance with the invention, a coupling is provided for connecting a ventilator tube to a tracheotomy tube. The ventilator tube has a connector at its leading end and the tracheotomy tube has a tapered tubular extension on its trailing end. The coupling is a preferably expandable, flexible tubular member with a first adapter on its trailing end for connecting its trailing end in a pneumatic flow path to the ventilator tube leading end connector and a second adapter on its leading end for mating its leading end in a pneumatic flow path with the trailing end of the tracheotomy tube. The second adapter has a latching mechanism for engaging the leading end of the coupling to the tracheotomy tube to prevent the leading end of the tubular member from axially displacing from the trailing end of the tracheotomy tube after they have been mated in the pneumatic flow path. An unlatching mechanism is provided for disengaging the latching mechanism from the tracheotomy tube so as to permit the leading end of the tubular member to axially displace from the trailing end of the tracheotomy tube. The unlatching mechanism is operated by non-axial forces so that the coupling can be disengaged from the tracheotomy tube without exertion of excessive axial force on the patient's neck.

Some known adult tracheotomy tubes have an inner cannula inserted into a trailing end of an outer cannula with the tubular extension on the trailing end of the inner cannula. For such tracheotomy tubes, the coupling tubular member has a first means on its leading end for mating the tubular member in the pneumatic flow path with the tubular extension of the inner cannula which is operable by motion of the mating means in a generally axial direction relative to the tubular extension. A second means is provided on the mating means for engaging with the outer cannula during mating to prevent the leading end of the tubular member from axially displacing from the tubular extension after mating. A third means is provided on the inner cannula for disengaging the engaging means from the outer cannula by application of force to the mating means in other than the generally axial direction to permit the leading end of the tubular member to axially displace from the tubular extension of the inner cannula. Typically, the trailing end of the outer cannula has opposed annular flanges and the engaging means consists of opposed means for resiliently snapping over the flanges. The disengaging means consists of means on the inner cannula for spreading the opposed flanges during rotational motion of the mating means about a longitudinal axis of the tubular member.

Other known adult tracheotomy tubes have an inner cannula inserted into a trailing end of an outer cannula with the tubular extension on the trailing end of the inner cannula. For such tracheotomy tubes, the coupling tubular member has a first means on a leading end of the tubular member for mating the tubular member in the pneumatic flow path with the tubular extension of the outer cannula by motion of the mating means in a generally axial direction relative to the tubular extension. A second means is provided on the mating means for engaging with the outer cannula during mating to prevent the tubular member from axially displacing from the tubular extension after mating. A third means is provided on the outer cannula which is operable by application of force on the mating means in a direction other than the generally axial direction for disengaging the engaging means from the outer cannula to permit the tubular member to axially displace from the tubular extension of the outer cannula. Typically, the trailing end of the outer cannula has annularly opposed flat notches. The disengaging means consists of means on the outer cannula for spreading the opposed flanges during rotational motion of the mating means about a longitudinal axis of the tubular member.

Known child tracheotomy tubes have a tubular extension on their trailing end. For such tracheotomy tubes, the coupling tubular member has a first means for mating the leading end of the tubular member in the pneumatic flow path with the tubular extension of the tracheotomy tube by motion of the mating means in a generally axial direction relative to the tubular extension. A second means is provided on the mating means for engaging with the tracheotomy tube to prevent the leading end of the tubular member from axially displacing from the tubular extension after mating. A third means is provided on the mating means which is operable by application of force on the mating means in other than the generally axial direction for disengaging the engaging means from the tracheotomy tube to permit the tubular member to axially displace from the tubular extension of the tracheotomy tube. The mating means consists of a nozzle insertable into the tubular extension. The engaging means consists of a clamshell, the clamshell and the tubular extension having complementary three-dimensional surfaces which prevent axial displacement of the clamshell from the tubular extension gripped therein. Half of the clamshell has diametrically opposite lugs and another half of the clamshell has diametrically opposite fingers which resiliently snap over the lugs when the clamshell is closed. The disengaging means consists of means on the fingers for spreading the fingers in response to inward radial pressure on the spreading means to release the lugs.

An improved child's tracheotomy tube has an arcuate soft tube cannula with a neck plate on its trailing end. The neck plate has a passageway aligned with the cannula passageway and an annular ring on its trailing side which extends the passageway. A tubular extension trails from the annular ring to further extend the passageway. Preferably, the tubular extension is formed using a soft inner tube and a hard outer sleeve permanently fused to the soft inner tube. The annular ring has at least one, and preferably three, circumferential sets of at least two displaced serrations in its outer wall.

Preferably, the serrations are equally displaced on the circumference, for example two diametrically opposed serrations, with corresponding serrations of each circumferential set being aligned on parallel diameters of the annular ring with the diameters being horizontal in relation to a vertical plane bisecting the arcuate cannula.

To connect the improved child's tracheotomy tube to a ventilator tube, the coupling provided has a tubular member adapted at its trailing end for connection in a pneumatic flow path to the ventilator tube leading end connector. The leading end of tubular member is adapted for mating the tubular member in the pneumatic flow path with the tubular extension of the tracheotomy tube by motion of the mating means in a generally axial direction relative to the tubular extension. The leading end of the tubular member is further adapted for engaging with one of the circumferential sets of serrations to prevent the leading end of the tubular member from axially displacing from the tubular extension after mating. The leading end of the tubular member is further adapted to be operable by application of force in other than the generally axial direction for disengaging the leading end of the tubular member from the engaged circumferential set of serrations to permit the leading end of the tubular member to be axially displaced from the tubular extension of the tracheotomy tube. Preferably, the trailing end adaptation of the tubular member is a hard annular ring on its trailing end, the ring having a tubular concentric rearward extension, a sleeve mounted for rotation on the extension and a stop mechanism on the extension for preventing the sleeve from axially displacing from the extension. This sleeve-on-extension configuration of the of the coupling allows rotational forces exerted on the tracheotomy system to be more likely dissipated at the ventilator end rather than the tracheotomy tube end of the system. Preferably, the leading end mating adaptation is a hard sleeve of inner diameter sized to axially receive the tracheotomy tube tubular extension with the trailing face of the tracheotomy tube extension abutting the trailing interior annular wall of the sleeve. Thus, axial motion is required only for initiation of abutting contact, reducing the likelihood of exertion of such axial force as might be required to create a frictionally tight locking fit. Preferably, the leading end engaging adaptation is a circumferential set of at least two fingers resiliently mounted on and oriented forward of the sleeve for seating in one of the circumferential sets of displaced serrations on the tracheotomy tube annular ring when the trailing face of the tracheotomy tube tubular extension abuts the trailing interior annular wall of the sleeve. Thus, the force exerted to engage the components is primarily radial rather than axial or rotational, reducing the likelihood of exertion of excessive axial force on the system. It is also preferred that disengaging adaptation be squeeze plates on the fingers for radially displacing the fingers to release them from the engaged set of serrations in response to radially inward pressure on the squeeze plates. Thus, the force exerted to disengage the components is also primarily radial rather than axial or rotational, reducing the likelihood of exertion of excessive axial force on the system.

A different embodiment of the coupling could be used to connect an air supply to any of a variety of respiratory support devices which are provided with radially outwardly extending flanges proximate their trailing end. The coupling would include the longitudinally flexing tubular member with a first adapter on its trailing end for connecting its trailing end in a pneumatic flow path to the air supply and a second adapter on its leading end for mating its leading end in the pneumatic flow path with the respiratory support device by motion of the second adapter in a generally axial direction toward the respiratory support device bringing a leading face of the flexing tubular member into abutment with a trailing face of a trailing end of the respiratory support device. A mechanism on the second adapter engages with the flanges of the respiratory support device when the flexing tubular member and the trailing face of the respiratory support device are in abutment, thus preventing the flexing tubular member from axially displacing from the respiratory support device. The engaging mechanism includes a mechanism co-operable with the respiratory support device flanges to disengage the engaging mechanism from the respiratory support device flanges by rotational movement of the second adapter relative to the respiratory support device, permitting the flexing tubular member to axially displace from the respiratory support device. Preferably, if an outer longitudinal wall of the respiratory support device is tapered, an inner longitudinal wall of the second adapter will be tapered so as to come into abutment with the tapered wall of the respiratory support device during mating of the coupling with the respiratory support device. Such a respiratory support device could, for example, be a tracheotomy tube outer cannula with radially outwardly extending flanges proximate its trailing end. In this application, the coupling would further include an inner cannula with a tubular extension on its trailing end with fingers resiliently pivoted on the perimeter of the tubular extension which will snap over the outer cannula flanges when a leading face of said tubular extension comes into abutment with a trailing face of the outer cannula. A pair of radially outwardly extending flanges angularly oriented between and trailing behind the fingers would be co-operable with the engaging mechanism of the second adapter of the coupling. The fingers prevent axial displacement of the inner cannula from the outer cannula and the engaging mechanism prevents the coupling from axially displacing from the inner cannula. The engaging mechanism includes a mechanism co-operable with the inner cannula flanges to disengage the engaging mechanism from the inner cannula flanges by rotational movement of the second adapter relative to the inner cannula tubular extension so as to permit the flexing tubular member to axially displace from the inner cannula tubular extension. The outer longitudinal wall of the inner cannula tubular extension and the inner longitudinal wall of the second adapter are preferably tapered so that they come into abutment during mating of the coupling with the inner cannula.

BRIEF DESCRIPTION OF THE DRAWINGS

Other objects and advantages of the invention will become apparent upon reading the following detailed description and upon reference to the drawings in which:

FIG. 5 is a top plan assembly view from the line 5-5 of FIG. 4;

FIG. 6 is a side elevation view of the assembled coupling and cannulas of FIGS. 1-3;

FIG. 7 is a perspective assembly view of the leading end adapter of the coupling of FIG. 3 and the outer cannula of FIG. 1;

FIG. 8 is a side elevation view of the assembled leading end adapter of the coupling of FIG. 3 and inner cannula of FIG. 2;

FIG. 9 is a trailing end elevation view of the assembly of FIG. 8;

FIG. 10 is a top plan view of the assembly of FIG. 8;

FIG. 11 is a leading end elevation view of the assembly of FIG. 8;

FIG. 12 is a leading end perspective view of the leading end adapter of the coupling of FIG. 3;

FIG. 13 is a trailing end perspective view of the leading end adapter of the coupling of FIG. 3;

FIG. 14 is a side elevation view of the leading end adapter of the coupling of FIG. 3;

FIG. 15 is a trailing end elevation view of the trailing end adapter of the coupling of FIG. 3;

FIG. 16 is a top plan view of the leading end adapter of the coupling of FIG. 1;

FIG. 25 is a side elevation assembly view of the cannulas and coupling of FIG. 19;

FIG. 26 is a side elevation view of the assembled cannulas and coupling of FIG. 19;

FIG. 29 is a leading end perspective view of the coupling of FIG. 27 in an open condition;

FIG. 30 is a leading end elevation view of the coupling of FIG. 27 in the open condition;

FIG. 31 is a top plan view of the leading end of the coupling of FIG. 27 in the open condition;

FIG. 32 is a side elevation view of the leading end of the coupling of FIG. 27 in the open condition;

FIG. 39 is a side elevation assembly view of the coupling of FIG. 37 and the assembled inner and outer cannulae of FIGS. 37 and 38;

FIG. 40 is a top plane assembly view of the coupling and inner cannula of FIG. 37;

Figure 1:
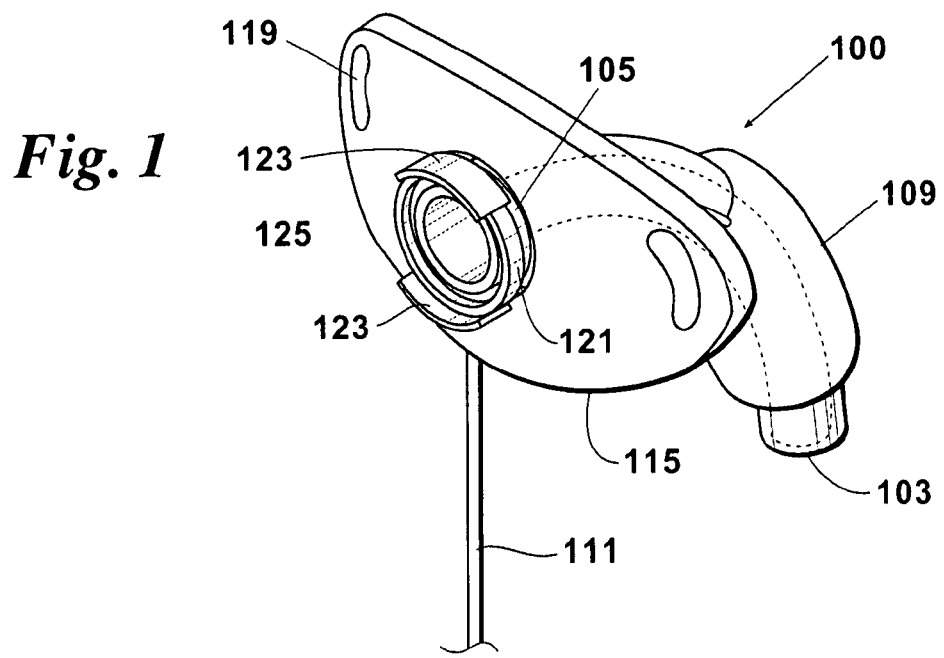
FIG. 1 is a perspective view of a first type of known tracheotomy tube outer cannula.
Figure 2:
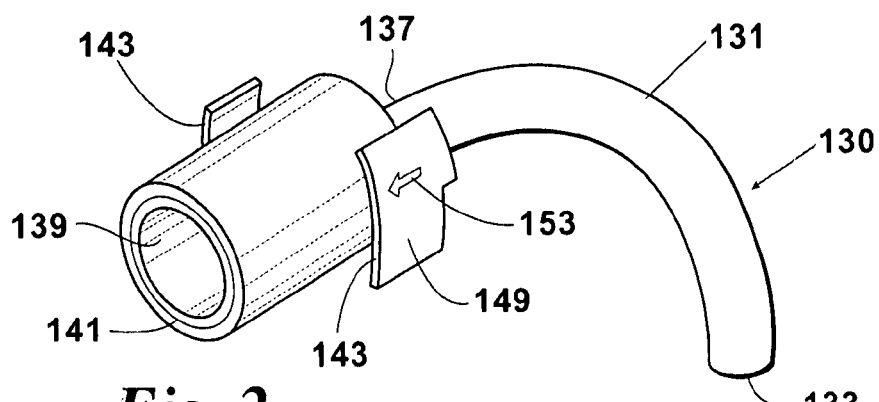
FIG. 2 is a perspective view of a first embodiment of an inner cannula for use with the outer cannula of FIG. 1.
Figure 3:
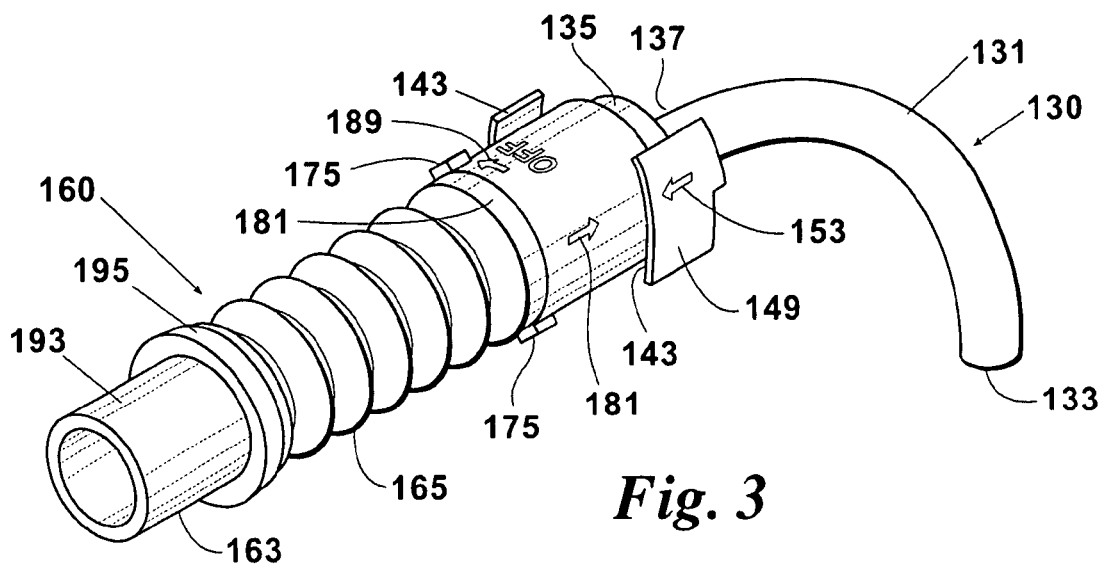
FIG. 3 is a perspective view of a first embodiment of a coupling connected to the inner cannula of FIG. 2.
Figure 4:
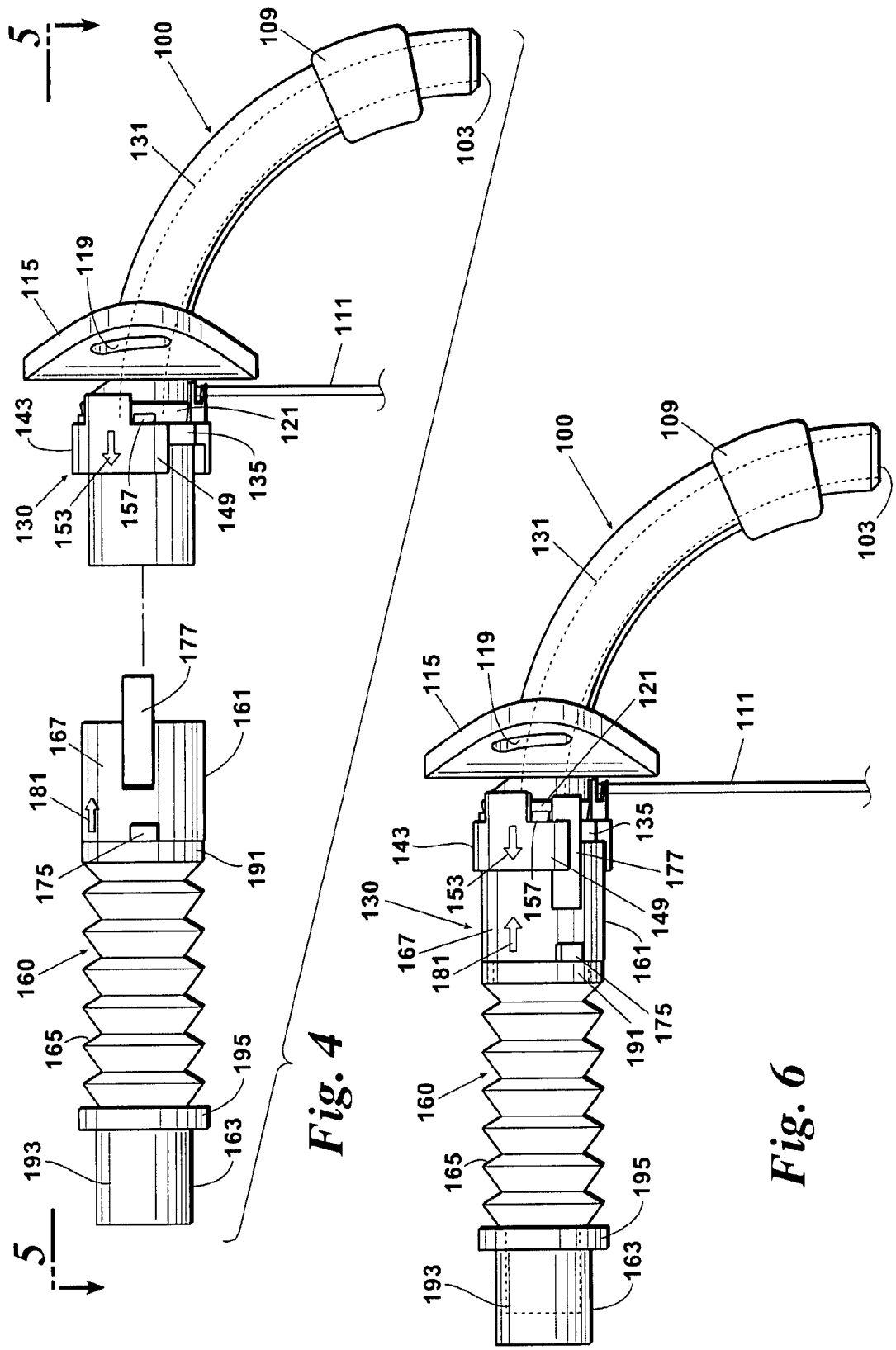
FIG. 4 is a side elevation assembly view of the coupling and cannulas of FIGS. 1-3.
Figure 17:
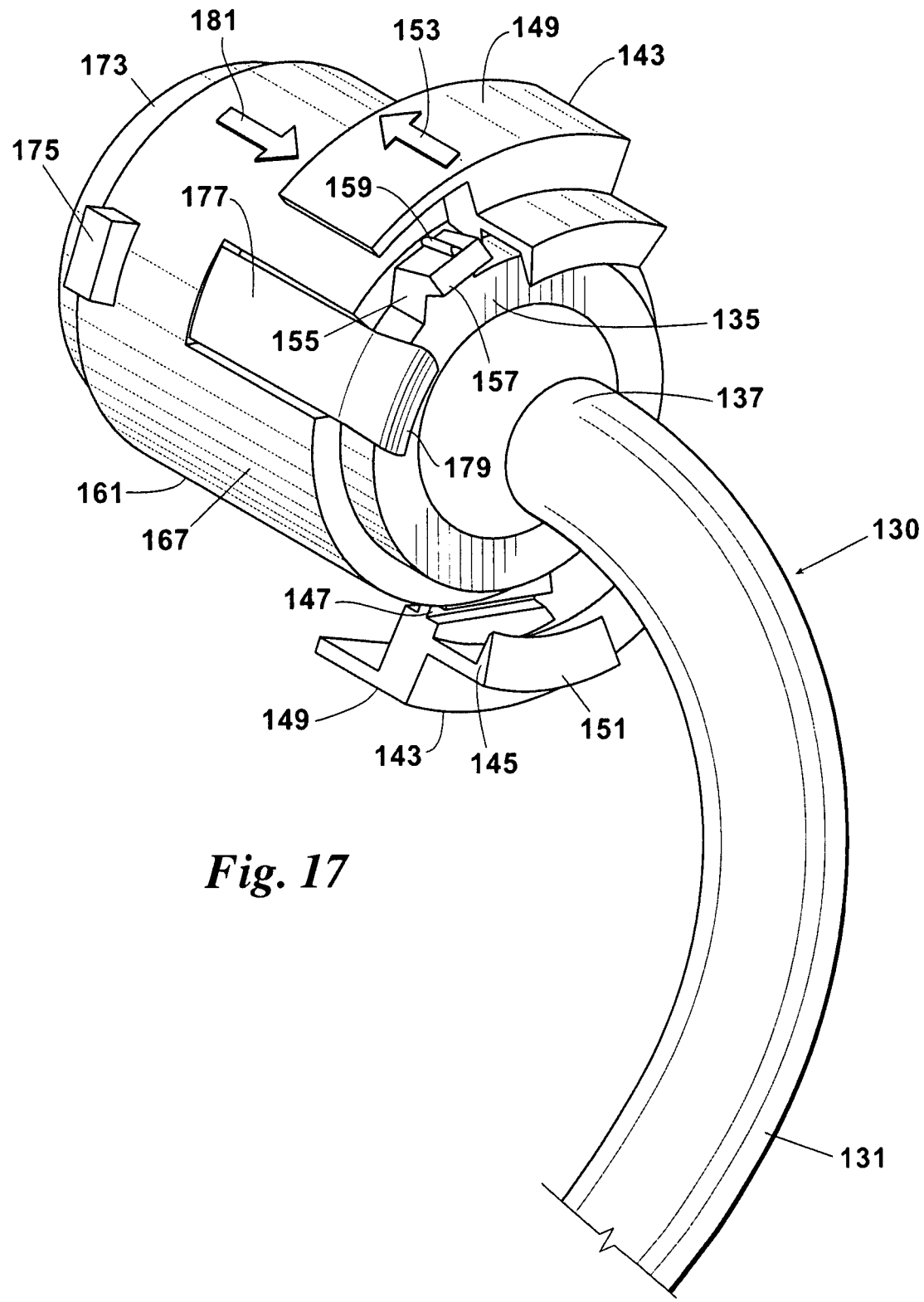
FIG. 17 is a leading end perspective view of the inner cannula of FIG. 2 and leading end adapter of the coupling of FIG. 3 in an operatively assembled condition.
Figure 18:
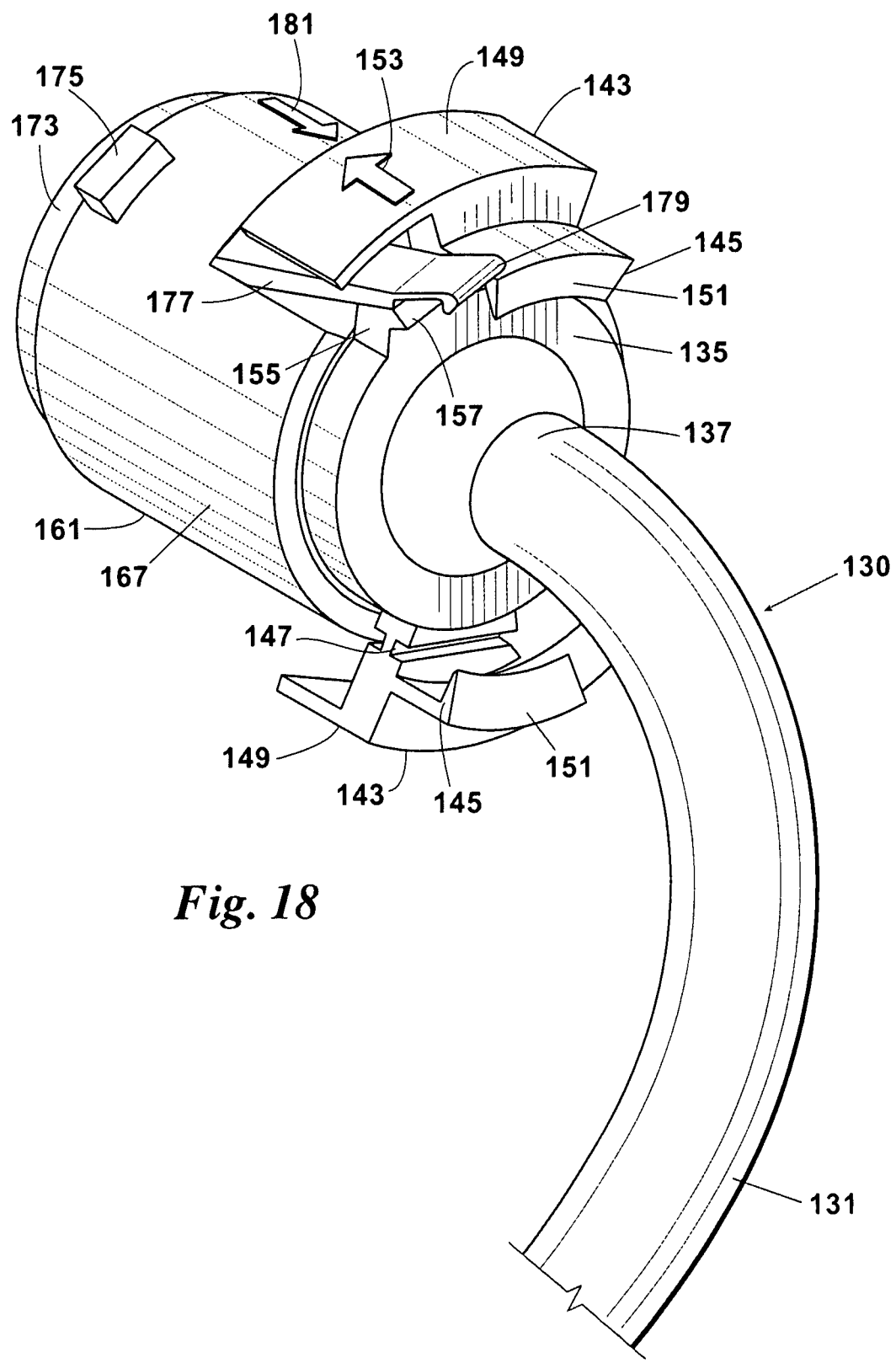
FIG. 18 is a leading end perspective view of the inner cannula of FIG. 2 and leading end adapter of the coupling of FIG. 3 in a ready-to-disconnect condition.
Figure 19:
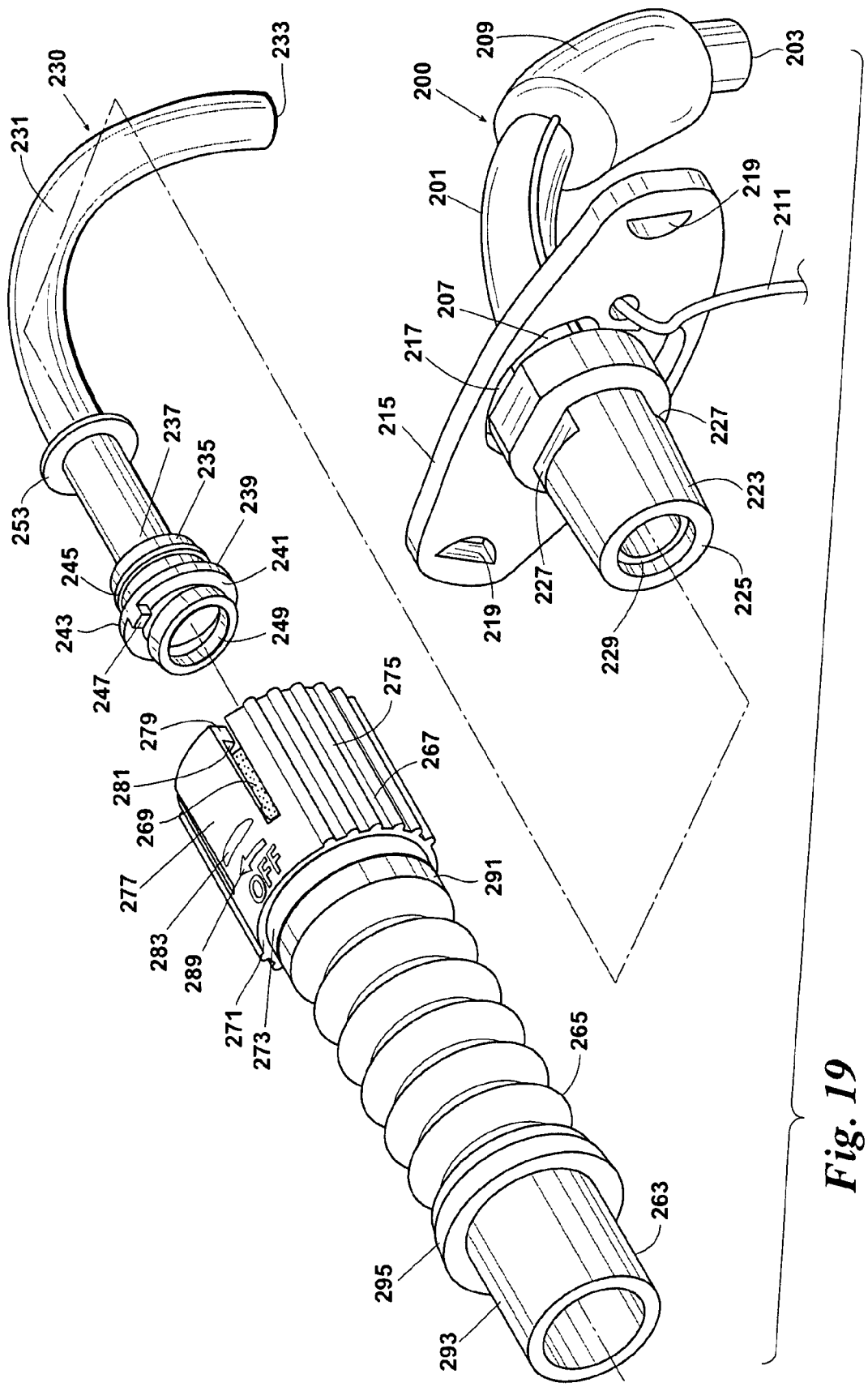
FIG. 19 is a perspective assembly view of a second embodiment of the coupling and inner cannula in relationship to a second type of known tracheotomy tube outer cannula.
Figure 20:
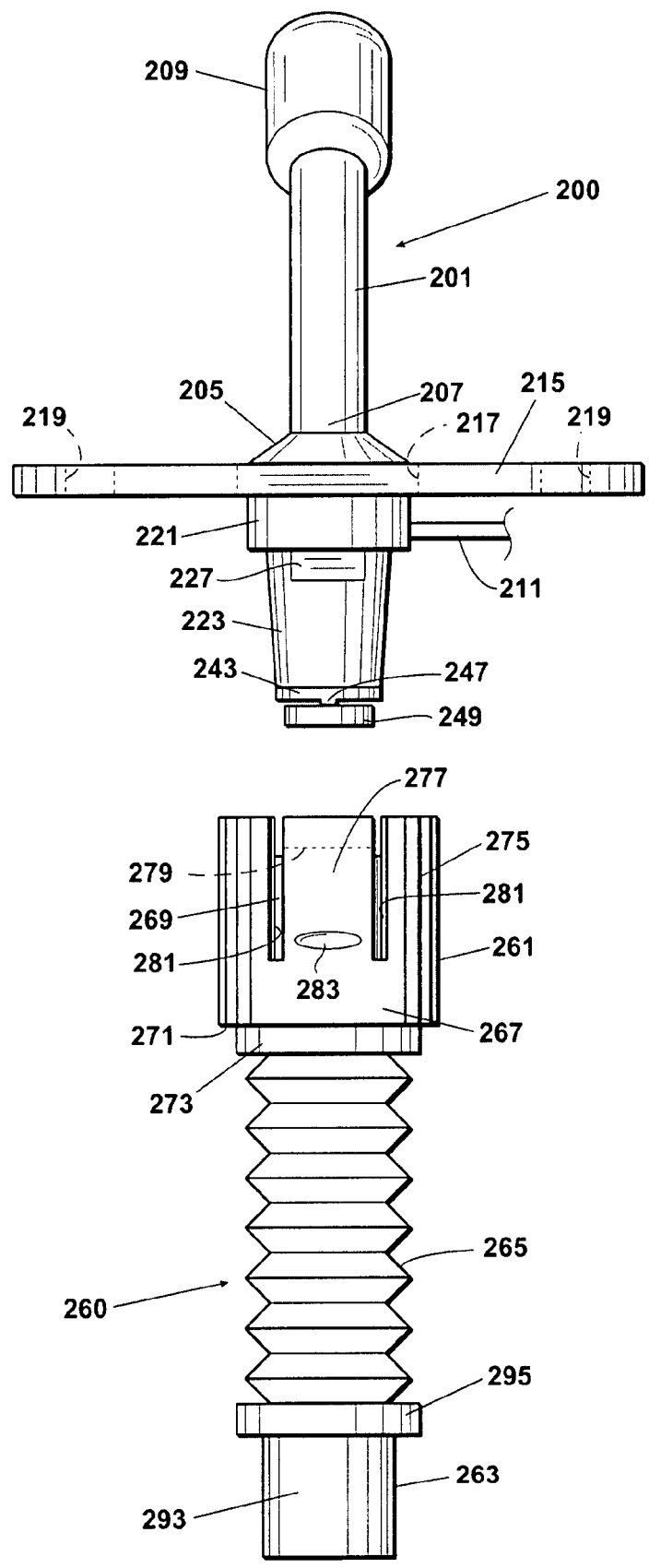
FIG. 20 is a top plan assembly view of the coupling and cannulas of FIG. 19.

While the invention will be described in connection with preferred embodiments thereof, it will be understood that it is not intended to limit the invention to those embodiments or to the details of the construction or arrangement of parts illustrated in the accompanying drawings.

DETAILED DESCRIPTION

Tracheal Inserts

Adult tracheotomy tubes are illustrated in FIGS. 1-18, showing a tracheotomy tube with outer and inner cannulas 100 and 130 and a tapered tubular extension 139 on the trailing end of the inner cannula 130 and FIGS. 19-26, showing a tracheotomy tube with outer and inner cannulas 200 and 230 and a tapered tubular extension 223 on the trailing end of the outer cannula 200. A child's tracheotomy tube is illustrated in FIGS. 27-35. A child's tracheotomy tube has only one cannula which, for purposes of explanation of the invention is identified as an outer cannula 300.

All three known outer cannulas 100, 200 and 300 are, in some respects, substantially similar, being arced tubes 101, 201 or 301 of approximately a quarter circle extending from a leading end 103, 203 or 303 to a collar 105, 205 or 305 at the trailing end 107, 207 or 307 of the arced tube 101, 201 or 301. A cuff 109, 209 or 309 on the leading half of the arced tube 101, 201 or 301 is inflatable via an air supply line 111, 211 or 311. The arced tube 101, 201 or 301 is the tracheal insert portion of the tracheotomy tube and, once inserted, the cuff 109, 209 or 309 is inflated to hold and seal the tube 101, 201 or 301 in position in the trachea. Each of the outer cannulas 100, 200 or 300 has a neck plate 115, 215 or 315 which positions the outer cannulas 100, 200 or 300 against the patient's neck and is adapted to maximize its manipulability relative to the collar 105, 205 or 305 by connecting hinges 117 or by openings 217 or contours 317 in its body. Each of the neck plates 115, 215 or 315 also has openings 119, 219 or 319 for connection of an adjustable strap to pass around and secure the neck plates 115, 215 or 315 against the patient's neck. The adult outer cannulas 100 and 200 are comparatively hard and the child's outer cannula 300 is very soft. From the collars 105, 205 and 305 on the trailing ends of the arced tubes 101, 201 and 301 toward the trailing ends of the outer cannulas 100, 200 and 300, the configurations of the outer cannulas 100, 200 and 300 are quite different.

Both inner cannulas 130 and 230 are also, in some respects, substantially similar, being arced tubes 131 or 231 of approximately a quarter circle extending from a leading end 133 or 233 to a collar 135 or 235 on a trailing end 137 or 237 of the arced tube 131 or 231. The inner cannulas 130 and 230 are inserted at their leading ends 131 and 231 into the trailing ends of their outer cannulas 100 and 200 until their trailing ends mate. From the collars 135 and 235 toward the trailing ends of the inner cannulas 130 and 230, the inner cannulas 130 and 230 are quite different.

The outer cannulas 100, 200 and 300 and their associated known inner cannulas have mechanisms which positively engage them against separation in their mated condition. They all present tapered tubular extensions for connection with known flexible connectors. The connection to known flexible connectors is universally accomplished by mere insertion of a tapered end of a tube into a constant diameter tube. The following illustrated embodiments of the outer cannulas 100, 200 and 300 are substantially the same as the known outer cannulas. The illustrated embodiments of the inner cannulas 130 and 230 and the flexible connectors or couplings 160, 260 and 360 are substantially different from the known inner cannulas and connectors so as to permit a positive engagement of the outer cannulas with their flexible connectors. However, they have been configured to work with the known outer cannulas 100, 200 and 300. The principles of the invention, however, are fully applicable to the connection of flexible connectors to outer cannulas other than those herein illustrated.

First Adult Tracheotomy Tube Embodiment

Looking now at FIGS. 1-18, the first type of adult tracheotomy tube is illustrated. As best seen in FIG. 1, the collar 105 on the outer cannula 100 has an annular ring 121 which is concentric about the trailing end 107 of the outer cannula tube 101 and has top and bottom quarter arcs 123 which extend concentrically on and in a trailing direction from the ring 121. A concentric groove 125 is also provided in the face of the trailing end 107 of the outer cannula tube 101.

Looking at FIGS. 1-3 and 8-11, the inner cannula 130 applies the principles of the invention to the outer cannula 100. A soft arced tube 131 extends upwardly and rearwardly from its leading end 133 to a hard collar 135 on its trailing end 137. The collar 135 tapers outwardly to a wider, concentric, hard, tapered tubular extension 139 which extends in a trailing direction from the collar 135. The extension 139 tapers toward its trailing end face 141. The collar 135 has a pair of diametrically opposed latches 143, as shown appearing at approximately the 2 and 8 o'clock orientations when looking at the trailing end face 141 of the inner cannula 130. The latches 143 have fingers 145 which extend radially inwardly therefrom for engagement against the trailing face of the annular ring 121 on the trailing end 103 of the outer cannula 100. The fingers 145 extend in the leading end direction from resiliently flexible supports 147 on the collar 135. Squeeze plates 149 extend in the trailing end direction from the fingers 145. The leading faces 151 of the fingers 145 are beveled so that, as the inner cannula 130 is inserted into the outer cannula 100 and the beveled faces contact the annular ring 121, the supports 147 flex to widen the distance between the fingers 145. Once the fingers 145 pass over the annular ring 121, the supports return to their unbiased condition in which the trailing faces of the fingers 145 engage the leading face of the ring 121, thus locking the inner cannula 130 in place on the outer cannula 100. The squeeze plates 149 provide suitable surfaces and leverage for the thumb and forefinger to apply pressure to flex the support 147 and spread the fingers 145 so that the fingers 145 can be disengaged from the annular ring 121. The squeeze plates 149 have alignment indicia such as arrows 153, as shown diametrically opposed and pointing in the trailing end direction. As best seen in FIGS. 6, 8, 9, 11, 17 and 18, the collar 135 also has diametrically opposed rotational and longitudinal ramps 155 and 157 and longitudinal beads 159 for reasons hereinafter explained.

Looking at FIGS. 1-16, the flexible connector 160 for use with the above outer and inner cannulas 100 and 130 has a leading end adapter 161, best seen in FIGS. 5, 7 and 12-15. The leading end adapter 161 has a hard outer sleeve 167 with a soft tube liner 169. The trailing end 171 of the sleeve 167 is of narrower diameter so as to provide a connecting ring 173 for reasons hereinafter explained. The outer sleeve 167 has diametrically opposed posts 175 on its wide circumference at the leading end of the connecting ring 173. A pair of diametrically opposed resiliently flexible arms 177 extend longitudinally from the sleeve 167 to radially inwardly extending fingers 179. The sleeve 167 also has alignment indicia such as arrows 181 pointing in the leading end direction. The flexible connector 160 is in proper rotational orientation for connection to the outer and inner cannulas 100 and 130 when the arrows 153 on the inner cannula 130 are aligned with the arrows 181 on the connector sleeve 167. As best seen in FIG. 6, when the arrows 153 and 181 are aligned, the connector arms 177 can pass under the squeeze plates 149 of the inner cannula latches 143 with the flexible connector fingers 179 at approximately the 4 and 10 o'clock orientations. This positions the connector fingers 179 on the clockwise side of the rotational and longitudinal ramps 155 and 157 when the connector 160 is connected to the outer and inner cannulas 100 and 130. The leading faces 183 of the connector fingers 179 are beveled so that, as the flexible connector 160 is moved longitudinally into the tapered tubular extension 139 of the inner cannula 130, the fingers 179 will be spread apart by and slide across the ring 121, on the outer cannula 100. Once the fingers 179 pass the ring 121 they resiliently close to secure the flexible connector 160 to the outer cannula 100. The inner cannula collar 135 is sandwiched between them.

As best seen in FIG. 12, the interior surfaces of the connector arms 177 are provided with longitudinal grooves 185 and the counterclockwise inside edges of the connector arms 177 are provided with longitudinal bevels 187. To remove the flexible connector 160 from the outer and inner cannulas 100 and 130, the connector 160 is rotated counterclockwise, as indicated by the rotational arrows 189, using the thumb and forefinger on the posts 175. As the connector 160 rotates, the longitudinal bevels 187 on the connector arms 177 ride on the rotational ramps 155 on the inner cannula collar 135 to unlatch the connector fingers 179 from the collar 135. The rotation is limited to the point of abutment of the inner cannula and connector fingers 145 and 179, whereupon longitudinal beads 159 on the inner cannula collar 135 and grooves 185 on the connector arms 177 engage to provide an audible click indicating that the connector 160 can be longitudinally displaced and disconnected from the outer and inner cannulas 100 and 130. As the connector 160 is withdrawn in the trailing direction, the connector fingers 179 ride on the longitudinal ramp 157 of the inner cannula collar 135 to assure that the connector fingers 179 cannot relatch during the process.

Second Adult Tracheotomy Tube Embodiment

Turning to FIGS. 19-26, the other type of adult tracheotomy tube is illustrated. The collar 205 of the outer cannula 200 has a hard annular ring 221 which is concentric about the trailing end 207 of the outer cannula tube 201. The hard tapered tubular extension 223 of the ring 221 narrows toward the trailing end 225. Top and bottom approximately quarter notches 227 are provided in the outer circumference of the tapered tubular extension 223 at the trailing end of the ring 221.

The inner cannula 230 applies the principles of the invention to the outer cannula 200. A soft arced tube 231 extends upwardly and rearwardly from its leading end 223 to a concentric collar 235 on its trailing end 237. A tapered tubular extension 239 extends in a trailing direction from the collar 235 to a trailing end face 241 of an annular ring 243 on the extension 239. The outside wall of the extension 239 has annular ridges 245 which complement the annular grooves 229 in the inside wall of the outer cannula tapered extension 223 to secure the inner cannula 230 in place in the outer cannula 200. A pair of vertically aligned studs 247 are provided on the trailing end face 241 of the inner cannula extension 239 for reasons hereinafter explained. A concentric pull ring 249 is hinged 251 to the bottom of the end face 241 of the extensions 239 to facilitate removal of the inner cannula 230 from the outer cannula 200. An annular outer flange 253 on the midportion of the inner cannula arced tube 231 helps to hold the inner cannula tube 231 concentrically within the outer cannula tube 201.

Figure 21:
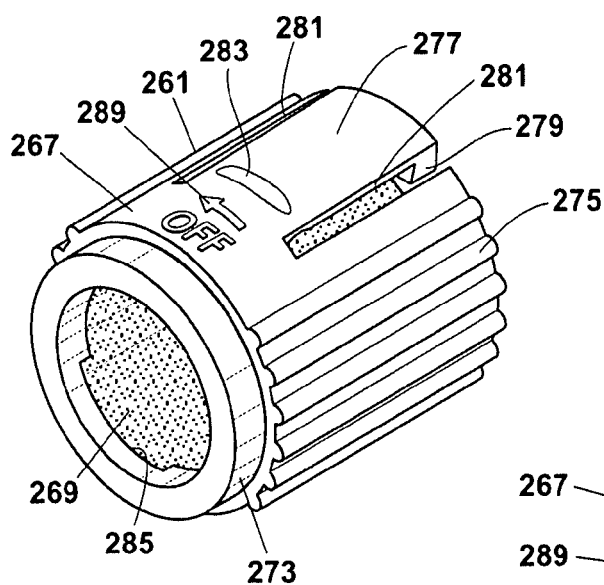
FIG. 21 is a trailing end view of the leading end of the coupling of FIG. 19.
Figure 24:
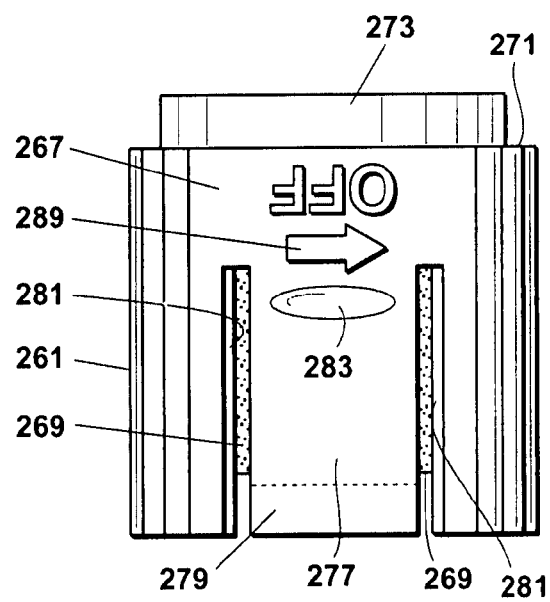
FIG. 24 is a top plan view of the leading end of the coupling of FIG. 19.
Figure 23:
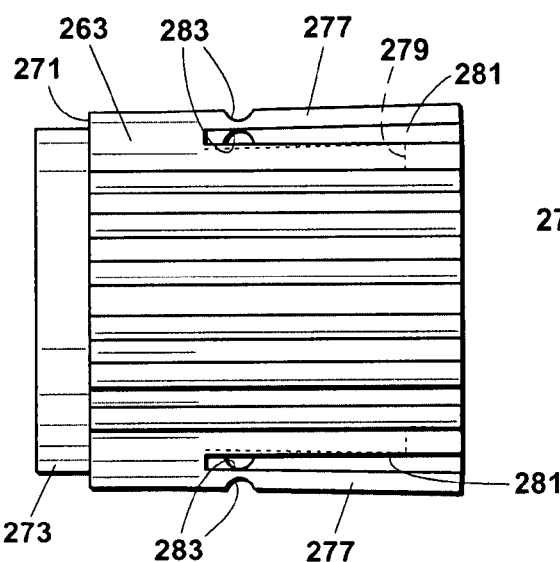
FIG. 23 is a side elevation view of the leading end of the coupling of FIG. 19.
Figure 22:
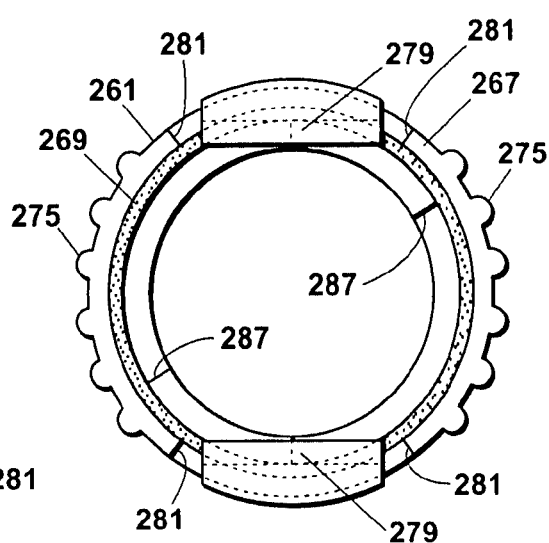
FIG. 22 is a leading end view of the leading end of the coupling of FIG. 19.

The flexible connector 260 for use with the above outer and inner cannulas 200 and 230 has a leading end adapter 261, best seen in FIGS. 21-24. The leading end adapter 261 has a hard outer sleeve 267 with a soft tube liner 269. The trailing end 271 of the sleeve 267 is of narrower diameter so as to provide a connecting ring 273 for reasons hereinafter explained. The outer sleeve 267 has a corrugated surface 275 to facilitate manipulation of the flexible connector 260. Diametrically vertically opposed arms 277 with radially inwardly extending fingers 279 at their leading ends are defined by longitudinal slots 281 in the sleeve 267. The fingers 279 are contoured to engage in the opposed notches 227 in the outer cannula tapered tubular extension 223. As best seen in FIG. 23, valleys 283 in the inner and outer surfaces of the arms 277 at their trailing ends permit the arms 277 to flex easily. As best seen in FIGS. 21 and 22, the leading face of the connecting ring 273 of the leading end adapter 261 has notches 285 which receive the studs 247 on the trailing end face 241 of the inner cannula 230. The notches 285 extend clockwise from the point of longitudinal insertion of the studs 247 to stops 287. Counterclockwise rotation of the leading end adapter 261 of the connector 260, indicated by the rotational arrows 289 on the sleeve 267, is terminated by the studs 247 striking the stops 287. At this point, the connector arms 277 will have flexed sufficiently to disengage the connector fingers 279 from the notches 227 in the outer cannula extension 223 so that the connector 260 can be longitudinally withdrawn from the outer and inner cannulas 200 and 230.

Child Tracheotomy Tube Embodiment

Figure 27:
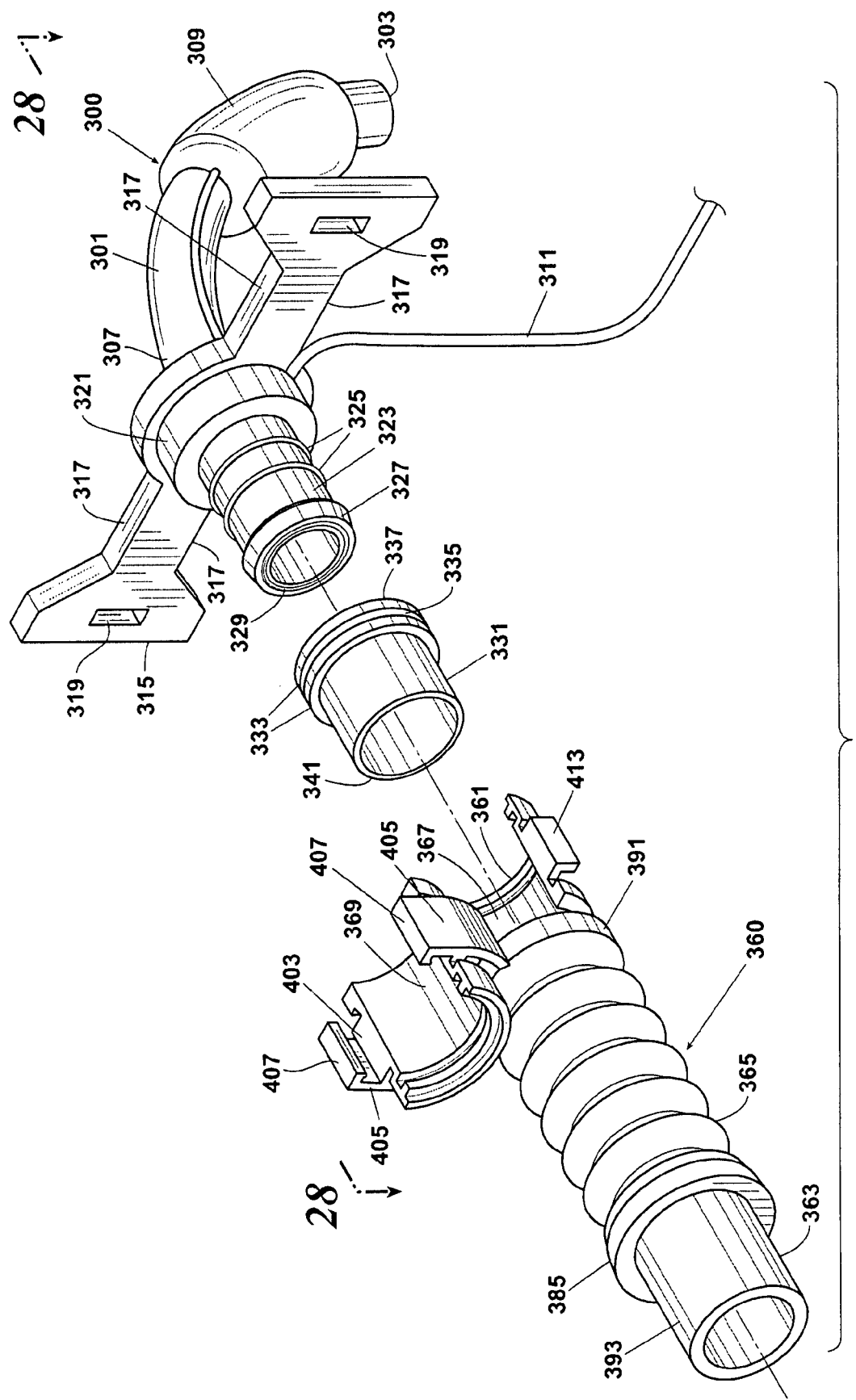
FIG. 27 is a perspective assembly view of a third embodiment of the coupling in relationship to a third type of known tracheotomy tube.
Figure 28:
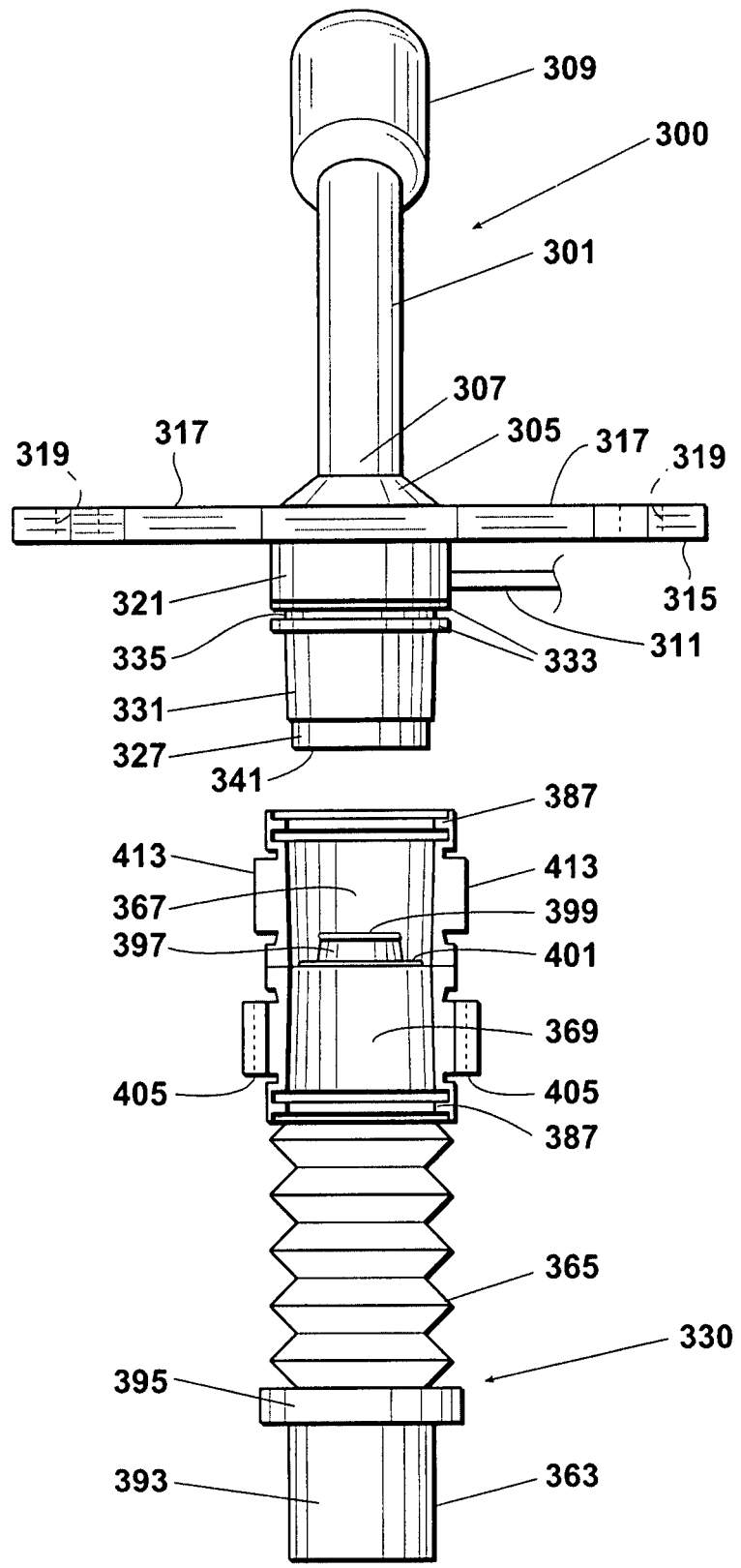
FIG. 28 is a top plan assembly view of the coupling and tracheotomy tube of FIG. 27.
Figure 33:
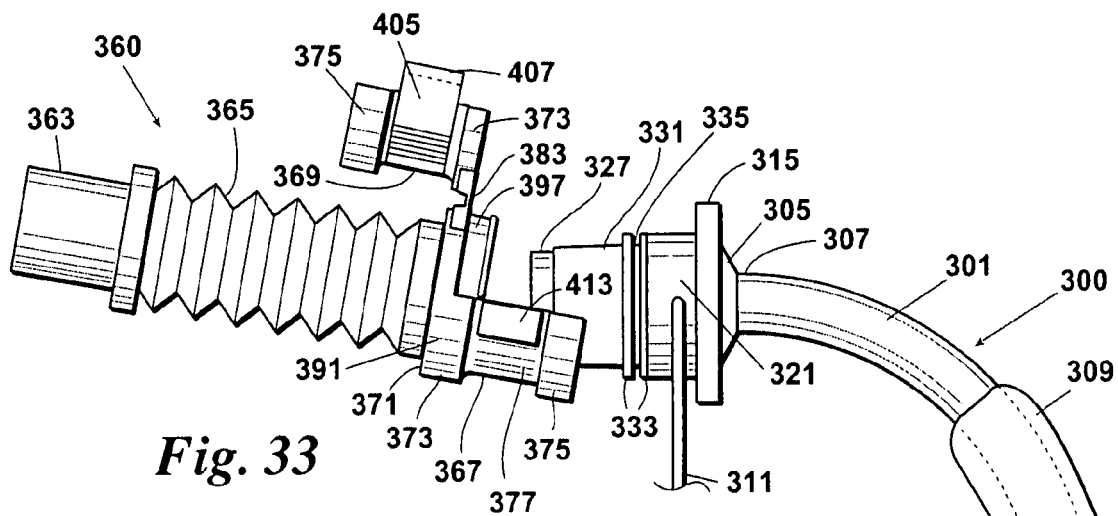
FIG. 33 is a side elevation assembly view of the coupling and tracheotomy tube of FIG. 27.
Figure 34:
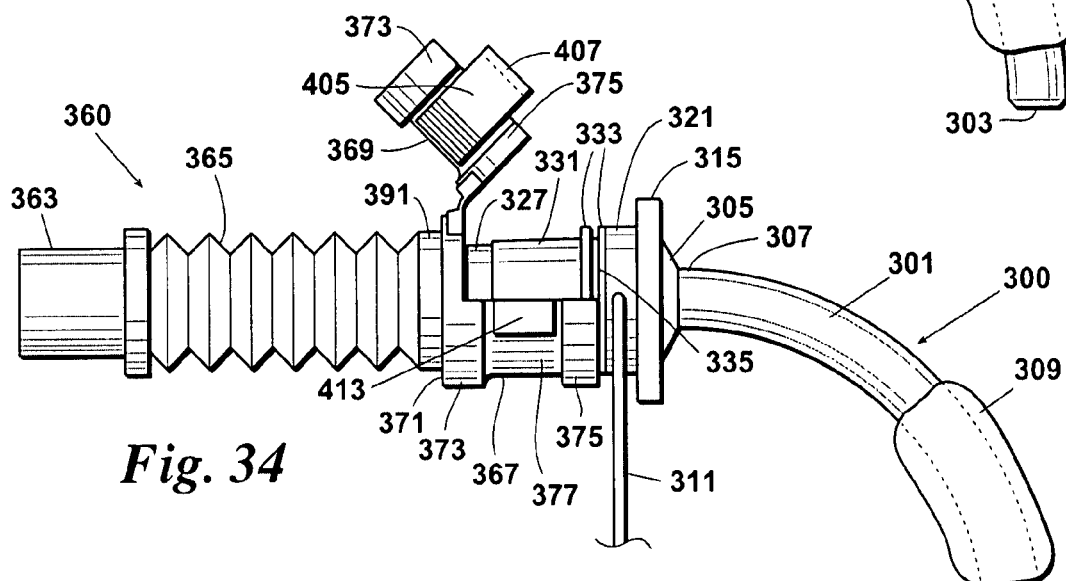
FIG. 34 is a side elevation view of the coupling and tracheotomy tube of FIG. 27 with the leading end of the coupling in the open condition.

Turning to FIGS. 27-35, the child's tracheotomy tube is illustrated. As best seen in FIG. 27, the collar 305 on the soft tube 301 has a concentric annular ring 321 extending in a trailing direction with a soft tapered extension 323 extending in a trailing direction from the ring 321. The extension 323 has annular ridges 325 in its circumference and a beveled flange 327 with an annular groove 329 in its trailing end face. A hard sleeve 331 is tapered to concentrically cover the tapered extension 323. The hard sleeve 331 has a pair of annular flanges 333 at its leading end defining an annular groove 335 therebetween. When the sleeve 331 is mounted on the soft tapered extension 323, the leading face 337 of the sleeve 331 abuts the trailing end face of the ring 321 on the collar 305 and the trailing end face 341 of the sleeve 331 abuts the leading end face of the beveled flange 327 on the tapered extension 323, locking the hard sleeve 331 in place on the soft extension 323.

Figure 35:
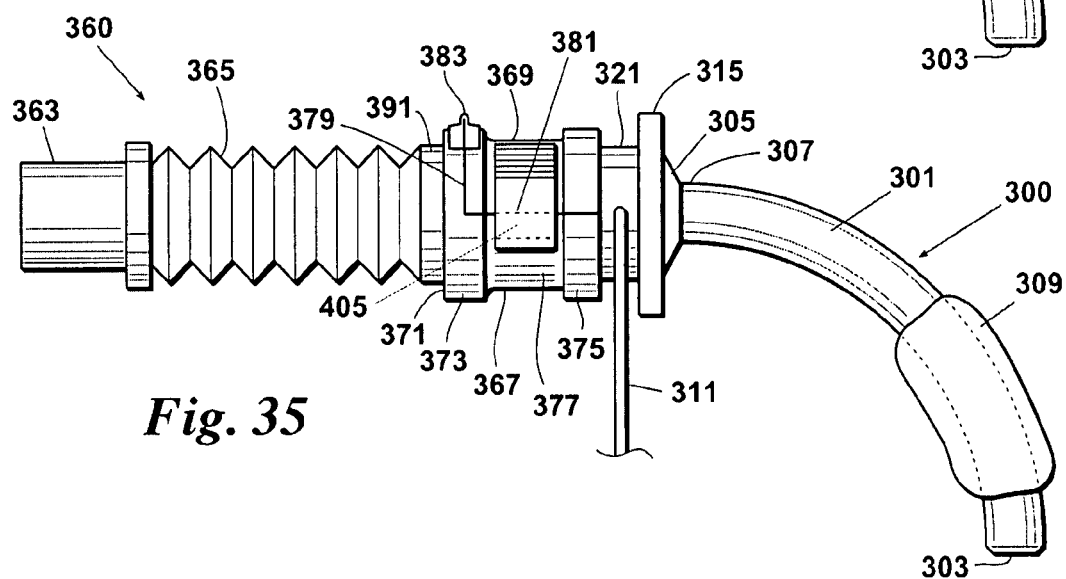
FIG. 35 is a side elevation view of the assembled coupling and tracheotomy tube of FIG. 27.

Looking at FIGS. 27-35, the flexible connector 360 for use with the cannula 300 has a leading end adapter 361, best seen in FIGS. 29-32. The leading end adapter 361 is a clamshell-type grip with bottom and top shells 367 and 369. The shells 367 and 369 extend from a trailing end face 371 on a trailing connecting ring 373 to a leading connecting ring 375 separated by a narrower body 377. As best seen in FIG. 35, the shells 367 and 369 are defined by a radial cut 379 splitting the top half of the trailing connecting ring 373 and a horizontal diametric cut 381 extending from the radial cut 379 through the leading connecting ring 375. The shells 367 and 369 are hinged 383 at the top of the radial cut 379. The leading connecting ring 375 has grooves 385 defining a ridge 387 which will engage in the groove 335 on the leading end of the hard sleeve 331 mounted on the soft tapered tubular extension 323 of the cannula 300. A tapered nozzle 397 extends in a leading direction from the leading face of the trailing connecting ring 373. The nozzle 397 has an annular bead 399 on the perimeter of its leading face. A concentric bead 401 is provided on the leading face of the trailing connecting ring 373 around the nozzle 397. The annular bead 399 on the nozzle 397 abuts the inside wall of the soft tapered tubular extension 323 of the cannula 300 and the concentric bead 401 on the leading connecting ring 375 seats in the groove 329 on the leading face on the beaded flange 327 of the soft tapered tubular extension 323 of the cannula 300 when the soft extension 323 with the hard sleeve 331 are longitudinally inserted into the clamshell of the connector 360. As best seen in FIGS. 29-32, flexibly resilient supports 403 extend radially outwardly from the top shell portion of the body 377 at the diametric cut 381. Arms 405 extend downwardly, considering the clamshell in the closed condition of FIG. 35, from each of the supports 403 to fingers 407 which extend diametrically inwardly from the arms 405. The fingers 47 have beads 409 on their upper inside edges. The arms 405 also extend upwardly from the supports 403 to corrugated squeeze plates 411 which aid in manually flexing the arms 405 between the thumb and forefinger. To cooperate with the fingers 407, L-shaped lugs 413 extend upwardly, again considering the clamshell in the closed condition of FIG. 35, from the bottom shell portion of the body 377 at the diametric cut 381. When the top shell 369 is closed on the bottom shell 367, the fingers 407 snap under the lugs 413 and the beads 409 engage the inside edges of the lugs 413 to assure a stable engagement.

The above described flexible connector 360 with the clamshell-type leading end adapter 361 accomplishes the objects, aims and advantages of the present invention when used with known outer cannula only or child tracheotomy tubes 300. Such single cannula tracheotomy tubes 300, however, have hereinbefore noted deficiencies of their own. In particular, looking at FIG. 27, the hard sleeve 331 replaces the manufacturer's original hard sleeve (not shown) which rotates on the soft extension 323 to allow some freedom of motion of the patient. This configuration focuses the dissipation of rotational forces at the patient end of the tracheotomy system. Moreover, the original and the replacement hard sleeve 331 are locked on the soft extension 323 by the beveled flange 337 and cannot be removed, for cleaning or other reason, without use of a tool and application of force to the tracheotomy tube and, consequently, the patient. Therefore, turning to FIG. 36, an improved child's tracheotomy tube 500 and connector 560 are illustrated which transfer the rotational capability to the connector 560, so that freedom of motion is maintained and the connector 560 can be disconnected from the tracheotomy tube 500 without applying rotational or longitudinal forces to the tracheotomy tube.

Figure 36:
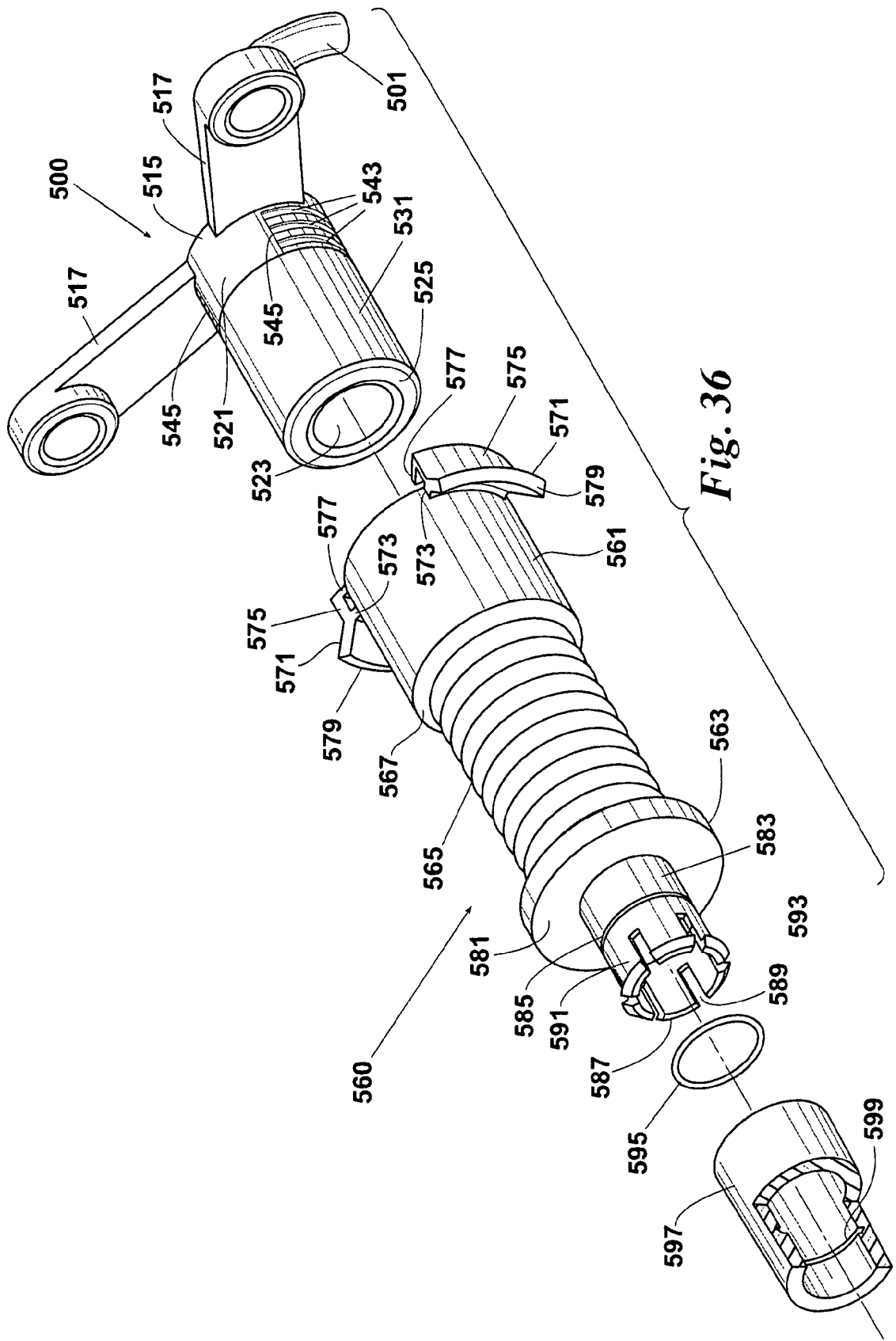
FIG. 36 is a perspective assembly view of an improved child's tracheotomy tube and associated coupling.

As seen in FIG. 36, the tracheotomy tube 500 is a unitary arrangement of a soft tube 501 formed by a silicone case on a coil of titanium or other non-iron based wire so that the improved tracheotomy tube 500 is compatible with MRI procedures. The soft tube 501 trails to a neck plate 515 with an annular ring 521 on its trailing side. A soft extension 523 trails concentrically from the annular ring 521 to a trailing annular flange 525 having the same diameter as the annular ring 521. Preferably, the soft extension 523 is covered up to the soft flange 525 by a hard sleeve 531 which is permanently fused to the soft extension 523. The annular ring 521 has a plurality of circumferential sets of diametrically opposed serrations 543, preferably and as shown transverse to and straddling the 3 and 9 o'clock diametric plane of the annular ring 521.

Continuing to look at FIG. 36, the flexible connector 560 has a leading end adapter 561 and a trailing end adapter 563 on the ends of an intermediate tube 565. The leading end adapter 561 is a hard sleeve with a trailing end annular wall 567. A pair of diametrically opposed latches 571 have flexible supports 573 which extend radially outwardly from the leading end adapter 561 to forwardly extending arms 575 with inwardly radially extending fingers 577. As shown, the latch fingers 577 straddle the 3 to 9 o'clock plane so as to be co-operable with the serrations 543 on the tracheotomy tube annular ring 521. This orientation is preferred so as to reduce the likelihood of the application of pressure by the chin and chest of the patient to the latches 571. The fingers 577 are engagable in the serrations 543 on the tracheotomy tube annular ring 521 to secure the connector 560 to the tracheotomy tube 500 when the soft flange 525 of the tracheotomy tube extension 523 is in abutment with the trailing end annular wall 567 of the leading end adapter 561. The walls 545 formed by the annular ring 521 at the ends of the serrations 543 prevent any significant rotation of the leading end adapter 561 in relation to the tracheotomy tube 500. The plurality of circumferential sets of serrations 543 allows tolerance for the lengths of the leading end adapter 561 and the tracheotomy tube extension 523. The latches 571 also have rearwardly extending squeeze plates 579 which provide suitable surfaces and leverage for the thumb and forefinger to apply pressure to flex the supports 573 and spread the latch fingers 577 so that the connector 560 can be disengaged from the tracheotomy tube 500 without need for exertion of excessive rotational or axial force on the tracheotomy tube 500.

The trailing end adapter 563 has a hard annular ring 581 on its leading end with a tubular concentric rearward extension 583. The extension 583 has an outer annular groove 585 on its mid-portion, an annular flange 587 on its outer trailing end and a plurality of slots 589 extending axially in its wall from its trailing end toward the groove 585 to provide a plurality of flexible fingers 591 with beveled tips 593. An O-ring 595 is seated in the groove 585. A sleeve 597 has a diameter suitable for sliding over the beveled tips 593 of the fingers 591 to radially depress the fingers 591 toward each other and receive the sleeve 597 fully on the extension 583. The sleeve 597 has an inner annular groove 599, preferably of cross-section which complements the cross-section of the beveled tips 593 on the trailing end of the sleeve 597. When the sleeve 597 is fully on the extension 583, the fingers 591 spread outwardly and the beveled tips 593 engage in the complemental groove 599 to prevent the sleeve 597 from sliding off the extension 583. The sleeve 597 is free to rotate on the extension 583, rotation being facilitated by the O-ring 595. The outer diameter of the sleeve 597 is tapered toward its trailing end to facilitate connection to the ventilator tube (not shown).

Third Adult Tracheotomy Tube Embodiment

Turning to FIGS. 37-45, an adult tracheotomy tube embodiment is illustrated which includes an inner cannula 630 and a flex connector 660 for use with an outer cannula 600 which is a modification of the outer cannula 100 of the first adult tracheotomy tube of FIGS. 1-18. Looking at FIG. 38, this modified outer cannula 600, similar in many respects to the outer cannula 100, has an arced tube 601 which extends from its leading end 603 to a collar 605, seen in FIG. 39, at its trailing end 607. On the collar 605 is an outer annular flange 609 with a trailing portion 611 and a leading portion 613. As best seen FIGS. 41 and 42, the leading portion 613 of the flange 609 has recessed upper and lower seats 615 and the flange 609 is divided into upper and lower portions defined by leaves 617 which extend outwardly from the flange 609 above and below the seats 615. Between the leaves 617, the flange 609 provides side seats 619.

The known inner cannula (not shown) presently used with the above-described known outer cannula 600 functions similarly to other known inner cannulae in that it is intended to be securely latched to the outer cannula 600 and to be and slip connected to the leading end of its ventilator tube connector. The slip connection is the result of longitudinal insertion of the trailing end of the inner cannula (not shown) into the leading end of the ventilator tube connector, the ventilator tube connector and the inner cannula being frictionally held in this relationship. Thus, the known combination of these inner and outer cannulae requires the exertion of longitudinal forces to create or terminate the frictional condition necessary to slip connect the inner cannula to the ventilator tube connector of the assembly and to separate them after they have been connected. Furthermore, this slip connection achieved by friction does not reduce the likelihood of inadvertent separation of the ventilator tube connector from the tracheotomy tube.

Figure 37:
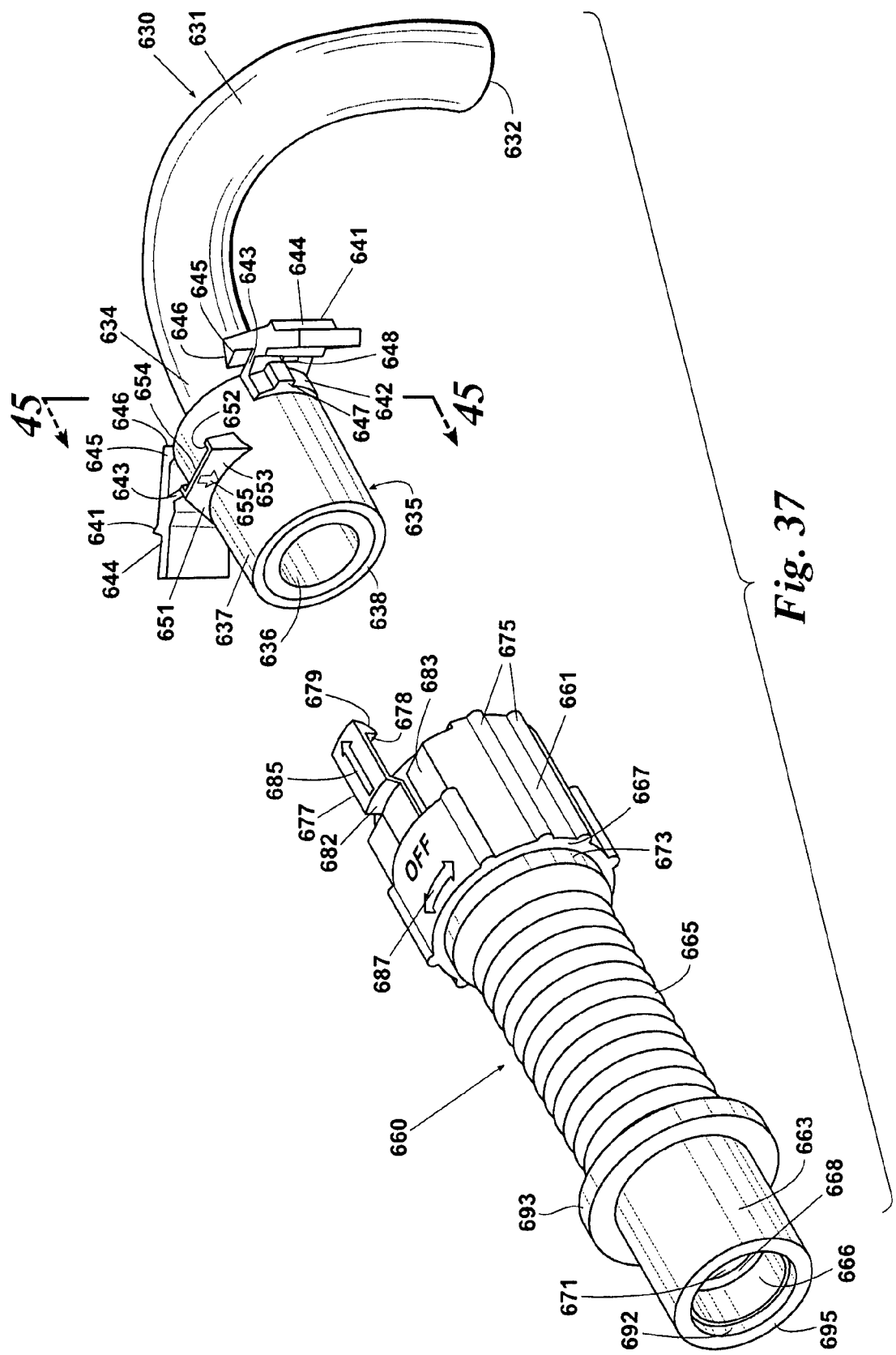
FIG. 37 is a perspective assembly view of a fourth embodiment of the coupling and an associated tracheotomy tube inner cannula.
Figure 38:
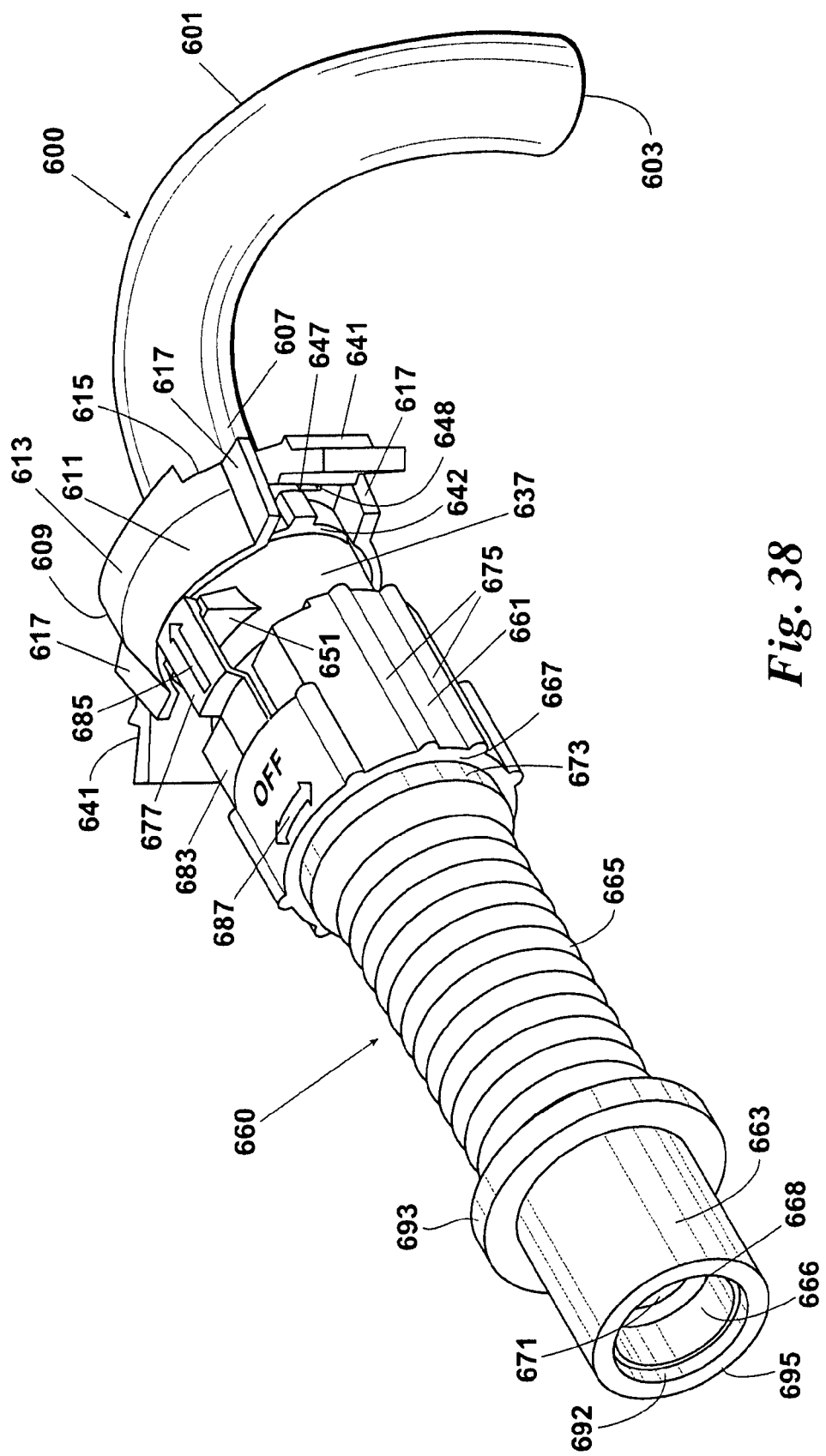
FIG. 38 is a perspective assembly view of the assembled coupling and inner cannula of FIG. 37 in association with a corresponding known tracheotomy tube outer cannula.
Figure 42:
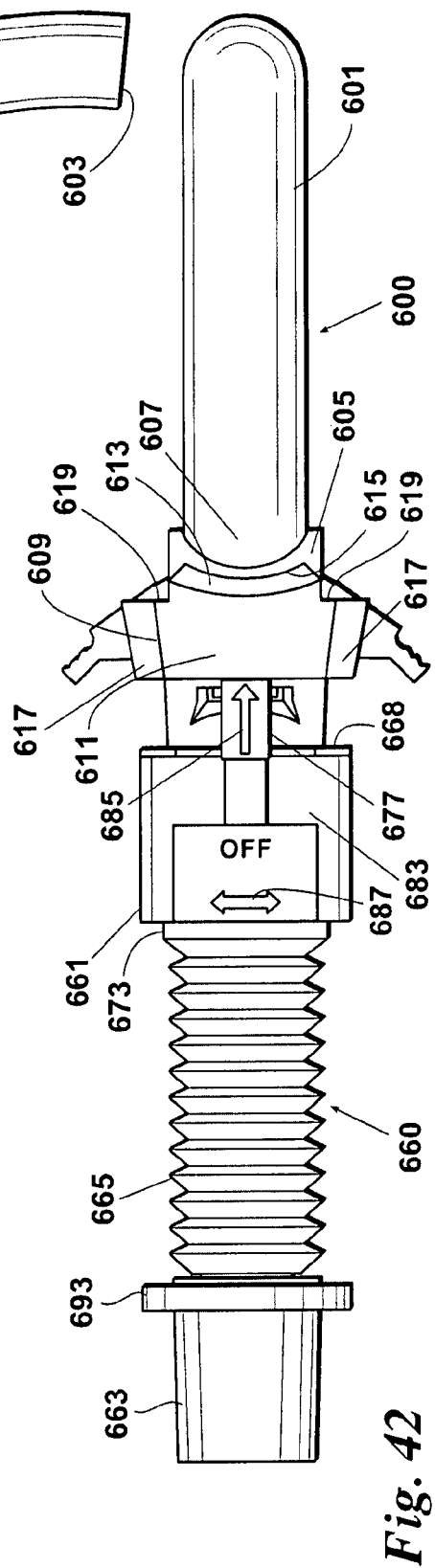
FIG. 42 is a top plane view of the assembled coupling and inner and outer cannulae of FIGS. 37 and 38.
Figure 44:
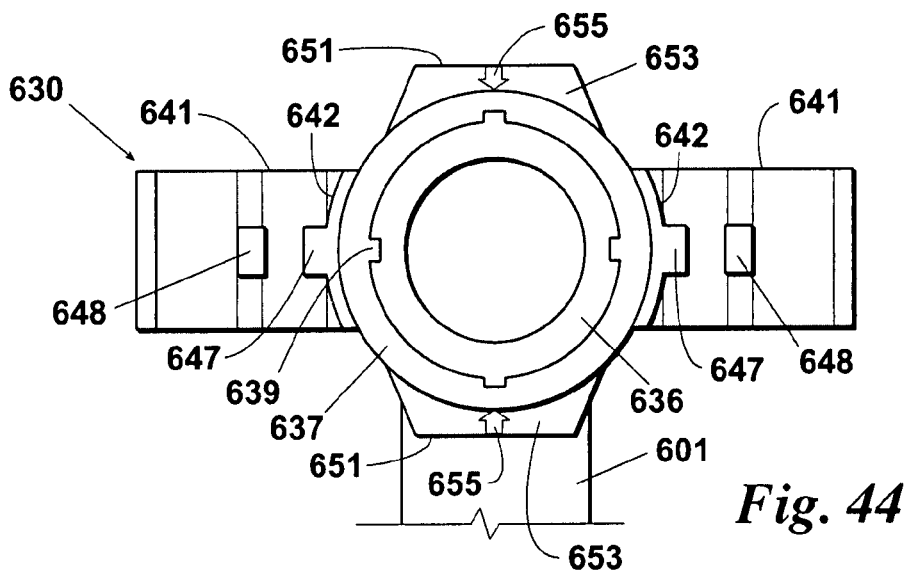
FIG. 44 is a cross-sectional view taken along the line 44-44 of FIG. 39.

Turning to FIG. 37, an improved inner cannula 630 for use with the outer cannula 600 is illustrated. The inner cannula 630 has an arced tube 631 extending from its leading end 632 to a collar 633, best seen in FIG. 40, at its trailing end 634. As seen in FIG. 37, the inner cannula 630 also has a tubular extension 635 at its trailing end 634. The extension 635 includes an inner soft sleeve 636 trailing from the collar 633. The soft sleeve 636 is contained within a hard outer sleeve 637, the outer surface of which is preferably narrowingly tapered from the collar 633 to its trailing end face 638. As best seen in FIG. 44, the inside wall of the hard outer sleeve 637 and the outside wall of the soft inner sleeve 636 have alternating splines and grooves 639 to prevent rotation of the hard outer sleeve 637 about the soft inner sleeve 636. Looking again at FIG. 37, the leading end of the hard outer sleeve 637 has a pair of opposed latches 641 for coupling the inner cannula 630 to the outer cannula 600. Each of the latches 641 has a base 642 on the outer wall of the hard sleeve 637 with a resiliently flexible post 643 which acts as a fulcrum for operation of the latch 641. Squeeze plates 644 extending rearwardly of the fulcrum 643 are used to manipulate fingers 645 which are contoured to engage with the side seats 619 on the outer cannula flange 609, as seen in FIG. 42. The leading faces 646 of the fingers 645 are beveled and the width of the squeeze plates 644 and fingers 645 is such that the latches 641 can be inserted between the opposed leaves 617 of the outer cannula flange 609, as seen in FIG. 38. The bases 642 of the latches 641 have outwardly extending posts 647 which are cooperable with strikers 648 which extend inwardly from the squeeze plates 644 to limit the stroke of the squeeze plates 644. When the cannulae 600 and 630 are connected, the leaves 617 on the outer cannula flange 609 limit rotation of the inner cannula 630 within the outer cannula 600 so that the inner and outer cannulae 600 and 630 cannot be separated inadvertently, but only by intentional operation of the latches 641 to release the outer cannula 600.

Figure 41:
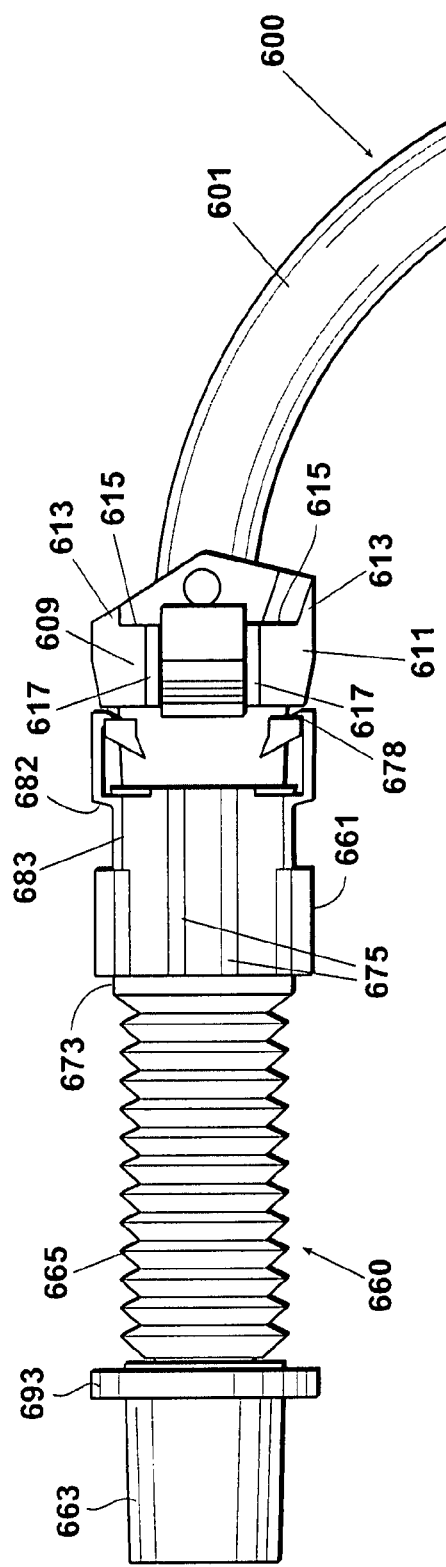
FIG. 41 is a side elevation view of the assembled coupling and inner and outer cannula of FIGS. 37 and 38.
Figure 45:
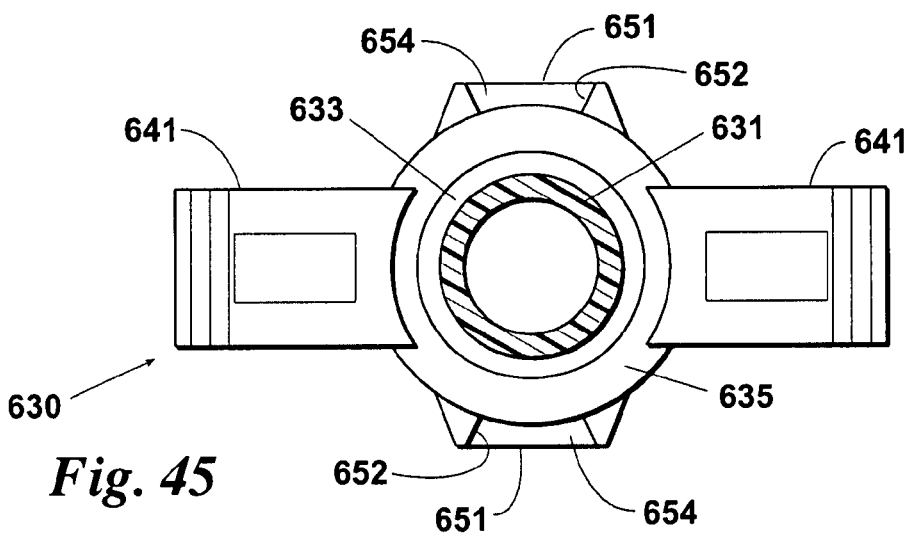
FIG. 45 is a cross-sectional view taken along the line 45-45 of FIG. 37.
Figure 46:
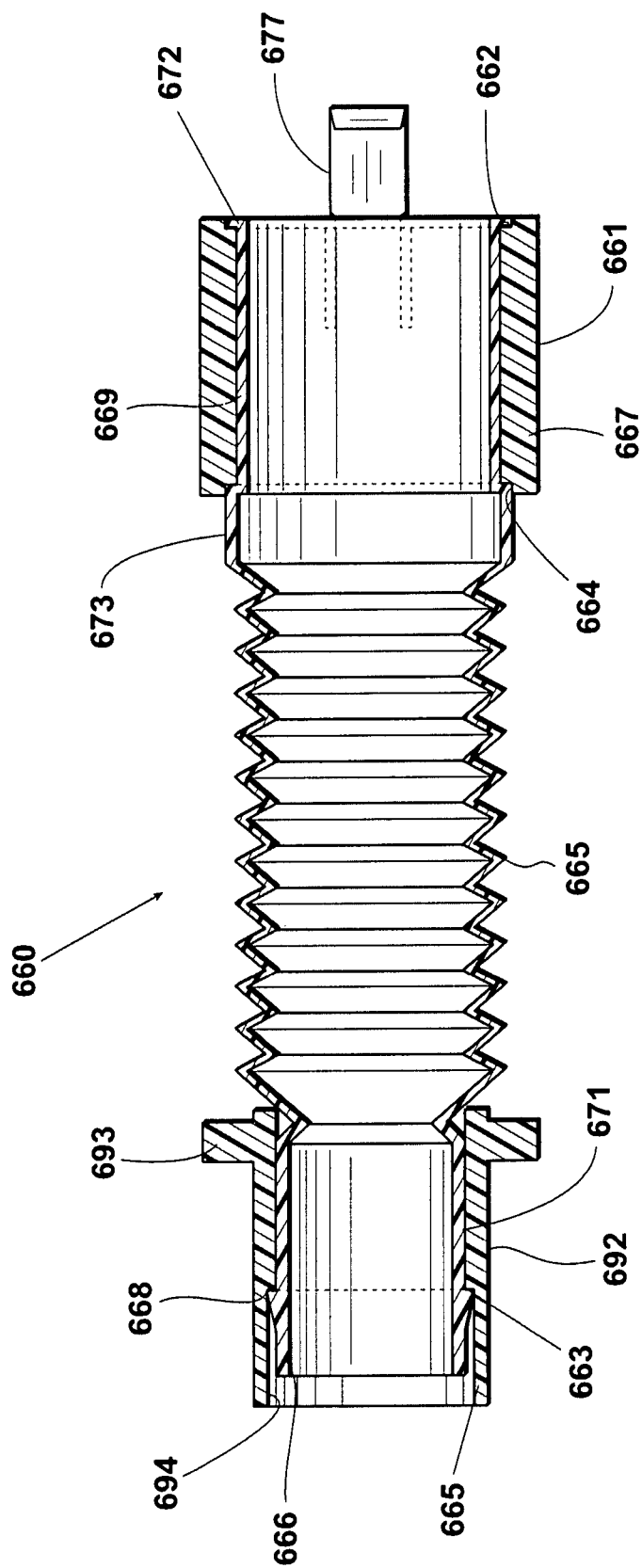
FIG. 46 is a cross-sectional view taken along a diametric plane of the coupling of FIG. 37.

As best seen in FIGS. 40, 41 and 45, the outer surface of the hard sleeve 637 of the inner cannula 630 has a pair of radially extending flanges 651, as shown angularly aligned between the latches 641 and positioned axially rearwardly thereof. Each of the inner cannula flanges 651 has side ramps 652 and a rear ramp 653 defining a U-shaped retaining seat 654. As best seen in FIG. 45, the side ramps 652 are tapered away from each other on the inside of the seat 654 and, as best seen in FIG. 39, the rear ramp 653 is tapered toward the leading end of the hard sleeve 637. Looking at FIG. 44, directional arrows 655 on the rear ramps 653 point axially to the rear centers of the rear ramps 653.

In FIGS. 37, 39 and 40, the flex connector 660 for use with the inner cannula 630 is shown disconnected from the inner cannula 630. As with the previously described connectors 160, 260, 360 and 560, the flexible connector 660 has a leading adapter 661, a trailing end adapter 663 and a tubular member 665 extending between the adapters 661 and 663.

The flex connector 660 has a leading end tubular portion 669 and a trailing end tubular portion 671 on opposite ends of the accordion-type flexing tubular member 665. The end portions 669 and 671 of the flexing tubular member 665 line the inside walls of the hard adapters 661 and 663. The leading end tubular portion 669 has an outer flange 672 on its leading rim and a wider outer diameter 673 proximate its trailing end. The trailing end tubular portion 671 has a trailing end portion 666 with an outer flange 668. The flexing tubular member 665 allows the connector 660 to expand and contract in accordion fashion and to bend up to approximately 90 degrees or more.

The leading end adapter 661 of the connector 660 is a hard sleeve 667 with annular seats 662 and 664 in its leading and trailing faces. The softer leading end tubular portion 669 is force fitted into the hard sleeve 667 and the outer annular flange 672 and wider diameter 673 on the end portion 669 engage in the annular seats 662 and 664 on the hard sleeve 667 to prevent the leading end adapter 661 from sliding off the leading end tubular portion 669 of the flex connector 660.

The trailing end adapter 663 of the connector 660 is a hard sleeve 692 with a leading outer annular flange 693 and a larger inner diameter 694 on its trailing portion 695. The trailing end adapter 663 is manipulable by use of the annular flange 693 on its hard sleeve 692 to press the hard sleeve 692 into the leading end of the ventilator tube. The flexing tubular member 665 allows this to be accomplished without exertion of undue axial force on the cannulae 600 and 630 or the patient. The softer trailing end tubular portion 671 is force fitted into the hard sleeve 692 and the annular flange 668 impinges upon the change in inner diameter 694 to prevent the trailing end adapter 693 from sliding off the trailing end tubular portion 671 of the flex connector 660.

Figure 43:
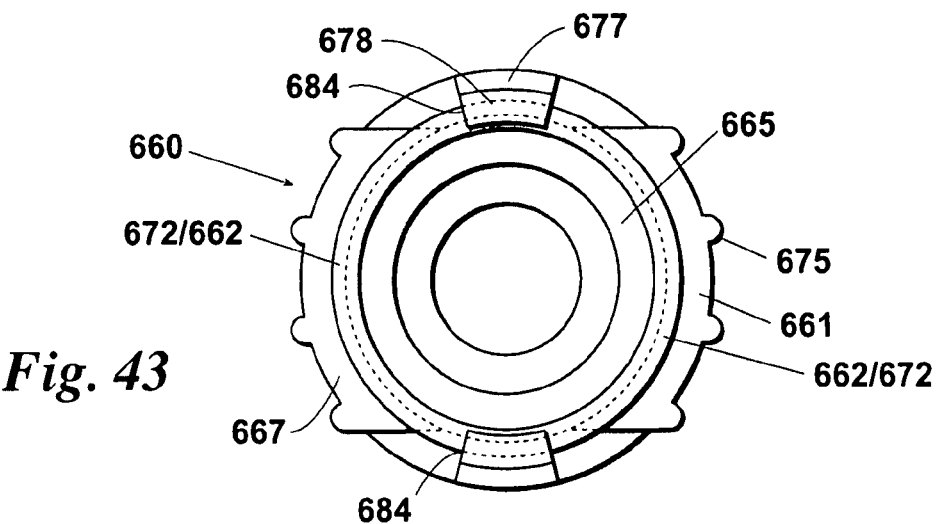
FIG. 43 is a cross-sectional view taken along the line 43-43 of FIG. 39.

The outer surface of the hard outer sleeve 667 of the leading end adapter 661 has a plurality of longitudinal ridges 675 to facilitate manipulation and rotation of the leading end adapter 661. A pair of resiliently flexible arms 677 extend forwardly of the leading end adapter 661 and are angularly positioned for alignment with the retaining seats 654 formed in the flanges 651 on the outer surface of the hard sleeve 637 of the inner cannula tubular extension 635. The arms 677 are fixed at one end on the hard outer sleeve 667 of the flex connector 660, extend longitudinally to posts 682 which space the arms 677 radially outwardly from the hard outer sleeve 667 and extend forwardly from the posts 682. As best seen in FIG. 39, the arms 677 have beveled leading faces 679 which are cooperable with the rear ramp 653 on the inner cannula tubular extension 635 to spread the arms 677 when the leading end adapter 661 is slipped onto the inner cannula tubular extension 635. The sidewalls 684 of the fingers 678 are also beveled, as best seen in FIG. 43. When the fingers 678 are engaged in the retaining seats 654 of the inner cannula flange 651, the beveled finger sidewalls 684 cooperate with the beveled interior side ramps 652 of the retaining seats 654 in the inner cannula flanges 651 and spread the arms 677 during rotation of the leading end adapter 661. Thus, disengagement of the flex connector leading end adaptor 661 from the inner cannula 630 is accomplished by use of rotational motion of the adapter 661.

As shown, the leading end adapter 661 has axial directional arrows 685 on its arms 677 which will align with the axial arrows 655 on the rear ramps 653 of the inner cannula flanges 651 when the fingers 678 are aligned to engage in the retaining seats 654. The leading end adapter 661 is also provided with rotational arrows 687 as a reminder that disengagement of the flex connector 660 from the inner cannula 630 is accomplished by exertion of rotational rather than axial forces on the leading end adapter 661.

The improved coupling 660 and its leading end adaptor 661 have been described in relation to connecting an inner cannula 630 to a ventilator tube. However, the coupling 660 could be used to connect any air supply to any of a variety of respiratory support devices if they are provided with radially outwardly extending flanges. Such devices include, but are not limited to, tracheotomy tube cannulae, endotracheal tubes, laryngeal mask apparatus, combitubes, airway pressure masks, resuscitation bags, and ventilator connectors such as elbows and step-up and step-down connectors and heat-moisture exchangers.

Common Connector Components

Each of the flexible connectors 160, 260, 360, 560 and 660 has its own unique leading end adapter 161, 261, 361, 561 and 661 as above described. The trailing end adapters 163, 263, 363 and 663 and intermediate tubes 165, 265, 365 and 665 for the flexible connectors 160, 260, 360 and 660, used with existing adult tracheotomy tubes 100, 200 300 and 600 are substantially the same. The trailing end adapters 163, 263, 363 and 663 have hard tubular extensions 193, 293, 393 and 693 with annular flanges 195, 295, 395 and 695 to facilitate manipulation of the connectors 160, 260, 360 and 660 during attachment to the ventilator. The trailing end adapters 161, 261, 361 and 661 are fixed to the trailing ends of their intermediate tubes 165, 265, 365 and 665, also as by ultrasonic welding.

The intermediate tube 565 used with the improved child's tracheotomy tube 500 is substantially the same as the intermediate tubes 165, 265, 365 and 665 of the other flexible connectors 160, 260, 360 and 660. The leading and trailing end adapters 561 and 563 are different.

Common Operational Features of the Embodiments

For each of the different tracheotomy tube outer cannulas 100, 200 and 300, the corresponding coupling 160, 260 and 360 has a leading end adapter 161, 261 and 361 which interlocks with its respective tracheotomy tube outer cannulas 100, 200 and 300 preventing them from inadvertently axially displacing from each other. However, non-axial force applied to the unlatching mechanism disengages the associated adapter 161, 261 or 361 from its tracheotomy tube outer cannula 100, 200 or 300 so that the coupling 160, 260 or 360 can be axially displaced without exertion of excessive axial force on the system and the patient.

Similarly, for the improved tracheotomy tube 500, its corresponding coupling 560 has a leading end adapter 561 which interlocks with its tracheotomy tube 500 to prevent them from inadvertently axially displacing from each other. However, non-axial force applied to the unlatching mechanism disengages them so that the coupling 560 can be axially displaced without exertion of excessive axial force on the system and the patient. While the improved tracheotomy tube 500 has been described as being intended for children, this designation is based on the heretofore accepted view that an adult tracheotomy tube has inner and outer cannulas and that a child's tracheotomy tube has a single cannula. However, the improved cannula 500 can be sized for use by children or adults.

For the third adult tracheotomy tube outer cannula 600, the corresponding coupling 660 has a leading end adapter 661 which interlocks with its tracheotomy tube inner cannula 630, preventing them from inadvertently axially displacing from each other. However, non-axial force applied to the unlatching mechanism disengages the adapter 661 from its tracheotomy tube inner cannula 630 so that the coupling 660 can be axially displaced without exertion of excessive axial force on the system and the patient.

Thus, it is apparent that there has been provided, in accordance with the invention, a ventilator to tracheotomy tube coupling that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. For connecting an air supply to a respiratory support device having radially outwardly extending flanges proximate a trailing end thereof, a coupling comprising:

a flexing tubular member;

means on a trailing end of said flexing tubular member for connecting said coupling in a pneumatic flow path to the air supply;

means on a leading end of said flexing tubular member for mating said coupling in said pneumatic flow path with the respiratory support device by motion of said means for mating in a generally axial direction toward the respiratory support device to bring a leading face of said flexing tubular member into abutment with a trailing face of a trailing end of the respiratory support device;

means on said means for mating for engaging with the flanges of the respiratory support device when said flexing tubular member and the trailing face of the respiratory support device are in abutment to prevent said flexing tubular member from axially displacing from the respiratory support device; and said means for engaging having means co-operable with the respiratory support device flanges for disengaging said means for engaging from the respiratory support device flanges by rotational movement of said means for mating relative to the respiratory support device so as to permit said flexing tubular member to axially displace from the respiratory support device.

2. For connecting an air supply to a respiratory support device having radially outwardly extending flanges proximate a trailing end thereof, a coupling comprising:

a flexing tubular member;

means on a trailing end of said flexing tubular member for connecting said coupling in a pneumatic flow path to the air supply;

means on a leading end of said flexing tubular member for mating said coupling in said pneumatic flow path with the respiratory support device by motion of said means for mating in a generally axial direction toward the respiratory support device to bring a leading face of said flexing tubular member into abutment with a trailing face of a trailing end of the respiratory support device;

means on said means for mating for engaging with the flanges of the respiratory support device when said flexing tubular member and the trailing face of the respiratory support device are in abutment to prevent said flexing tubular member from axially displacing from the respiratory support device; and said means for engaging having means co-operable with said inner cannula flanges for disengaging said means for engaging from said inner cannula flanges by rotational movement of said means for mating relative to said inner cannula tubular extension so as to permit said flexing tubular member to axially displace from said inner cannula tubular extension.

* * * * *